(12) United States Patent
Pan

(10) Patent No.: US 8,492,356 B2
(45) Date of Patent: Jul. 23, 2013

(54) METHODS OF INHIBITING TUMOR GROWTH USING TTK ANTAGONISTS

(75) Inventor: Guohua Pan, Oakville (CA)

(73) Assignee: University Health Network, Toronto (CA)

( * ) Notice: Subject to any disclaimer, the term of this patent is extended or adjusted under 35 U.S.C. 154(b) by 231 days.

(21) Appl. No.: 12/808,159

(22) PCT Filed: Dec. 19, 2008

(86) PCT No.: PCT/CA2008/002228
§ 371 (c)(1),
(2), (4) Date: Sep. 3, 2010

(87) PCT Pub. No.: WO2009/079768
PCT Pub. Date: Jul. 2, 2009

(65) Prior Publication Data
US 2011/0002923 A1 Jan. 6, 2011

Related U.S. Application Data

(60) Provisional application No. 61/008,649, filed on Dec. 21, 2007.

(51) Int. Cl.
*C12N 15/11* (2006.01)
*A61K 39/00* (2006.01)
(52) U.S. Cl.
USPC ..................................... 514/44 A; 424/184.1

(58) Field of Classification Search
USPC ..................................... 514/44 A; 424/184.1
See application file for complete search history.

(56) References Cited

FOREIGN PATENT DOCUMENTS
WO   WO 02/068444 A1   9/2002

OTHER PUBLICATIONS

D. J. Slamon et al., "Use of Chemotherapy Plus a Monoclonal Antibody Against HER2 for Metastatic Breast Cancer That Overexpresses HER2," The New England Journal of Medicine, vol. 344, No. 11, Mar. 5, 2001, pp. 783-792.
Bibo Yuan et al., "Increased Expression of Mitotic Checkpoint Genes in Breast Cells with Chromosomal Instability," Clinical Cancer Research, vol. 12, No. 2, Jan. 15, 2006, pp. 405-410.
International Search Report mailed Feb. 11, 2009, received in PCT/CA2008/002228.

*Primary Examiner* — Brian Whiteman
(74) *Attorney, Agent, or Firm* — McCarter & English, LLP; Steven G. Davis; Wei Song

(57) ABSTRACT

The present invention relates to methods for treating TTK positive breast cancers or soft-tissue sarcomas in a mammalian subject by administering a therapeutically effective amount of a TTK antagonist. The invention also provides compositions comprising a TTK antagonist and a HER-2 antagonist, as well as methods of diagnosing a basal-like breast cancer and methods of determining the prognosis of a subject having a cancer by assessing expression of TTK in a tumor sample from a subject.

16 Claims, 19 Drawing Sheets

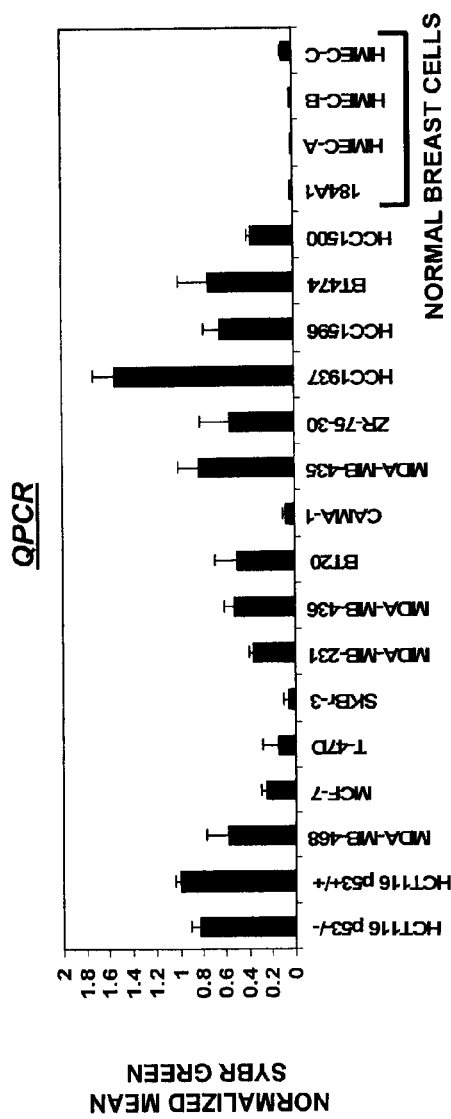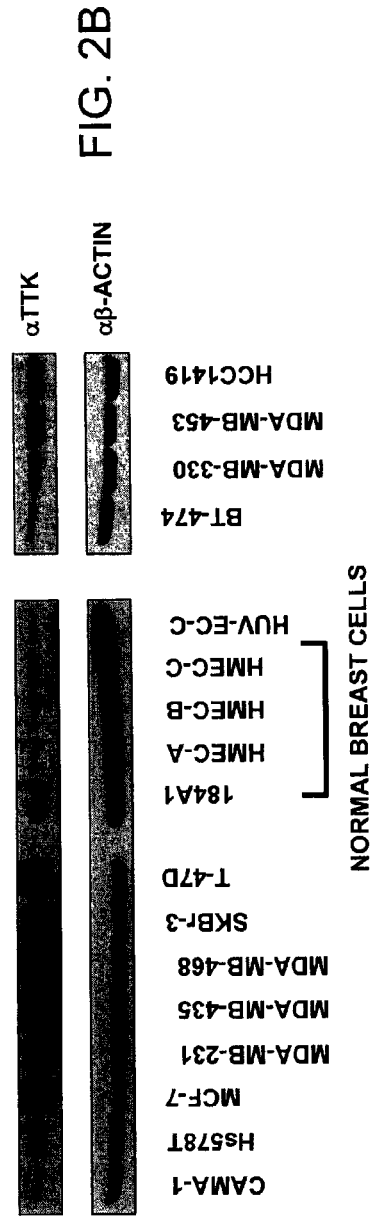

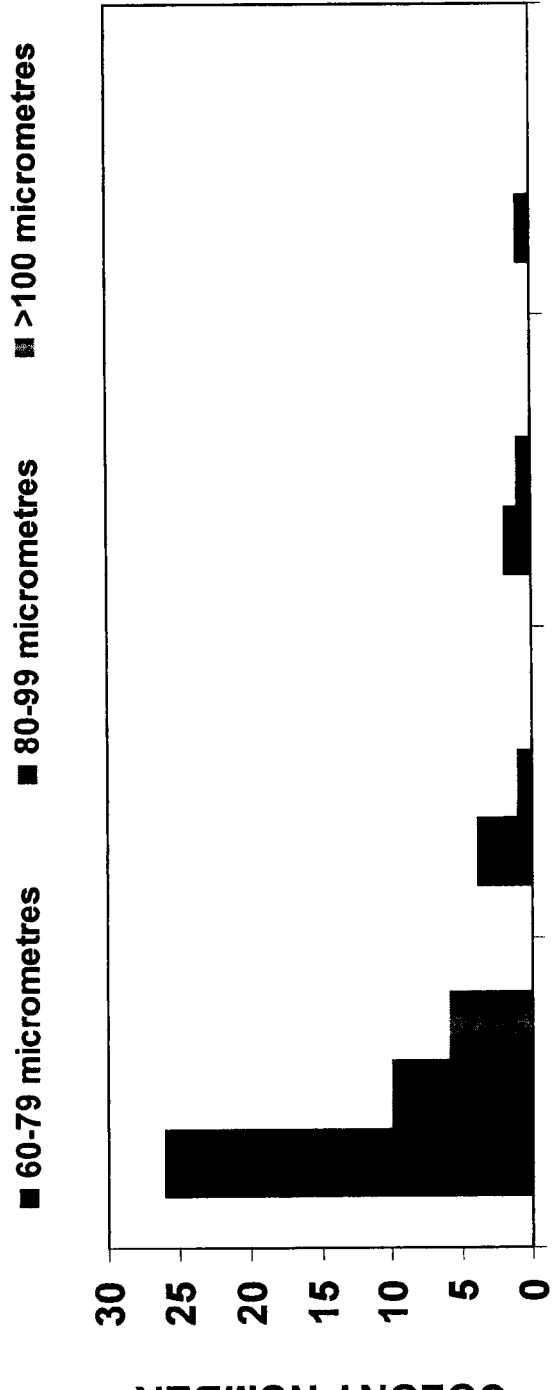
FIG. 11A
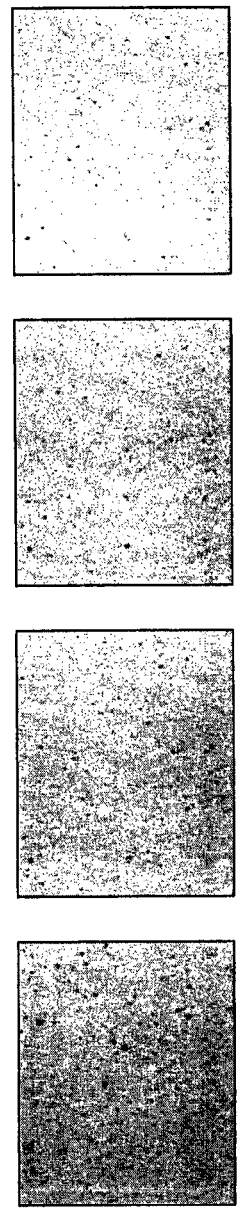
FIG. 11E
FIG. 11D
FIG. 11C
FIG. 11B

```
   1 ggaattcctt tttttttttt tttgagatgg agtttcactc ttgttggcca ggctggagtg
  61 caatggcaca atctcagctt actgcaacct ccgcctcccg ggttcaagcg attctcctgc
 121 ctcagcctct caagtagctg ggattacagg catgtgccac caccectggc taactaattt
 181 cttttctatt tagtagagat ggggtttcac catgttggtc aggctggtct tgaactcctg
 241 acctcaggtg atccacttgc cttggcctcc caaagtgcta ggattacagc cgtgaaactg
 301 tgcctggctg attcttttt tgttgttgga ttttgaaac agggtctccc ttggtcgccc
 361 aggctggagt gcagtggtgc gatcttggct cactataacc tccacctcct ggtttcaagt
 421 gatcctccca ctttagcctc ctgagtagct gtgattacag gcgtgcacca ccacccggg
 481 ctaattttg tatttttatt agagacaggg tttcaccatg ttggccaggc tgttctcaaa
 541 ctcctggact caagggatcc gcctgcctcc acttcccaaa gtcccgagat tacaggtgtg
 601 agtcaccatg cctgacctta taattcttaa gtcattttt ctggtccatt tcttccttag
 661 ggtcctcaca acaaatctgc attaggcggt acaataatcc ttaacttcat gattcacaaa
 721 aggaagatga agtgattcat gatttagaaa ggggaagtag taagcccact gcacactcct
 781 ggatgatgat cctaaatcca gatacagtaa aaatgggta tgggaaggta gaatacaaaa
 841 tttggtttaa attaattatc taaatatcta aaaacatttt tggatacatt gttgatgtga
 901 atgtaagact gtacagactt cctagaaaac agtttgggtt ccatcttttc atttccccag
 961 tgcagttttc tgtagaaatg gaatccgagg atttaagtgg cagagaattg acaattgatt
1021 ccataatgaa caaagtgaga gacattaaaa ataagtttaa aaatgaagac cttactgatg
1081 aactaagctt gaataaaatt tctgctgata ctacagataa ctcgggaact gttaaccaaa
1141 ttatgatgat ggcaaacaac ccagaggact ggttgagttt gttgctcaaa ctagagaaaa
1201 acagtgttcc gctaagtgat gctctttaa ataaattgat tggtcgttac agtcaagcaa
1261 ttgaagcgct tcccccagat aaatatggcc aaaatgagag ttttgctaga attcaagtga
1321 gatttgctga attaaaagct attcaagagc cagatgatgc acgtgactac tttcaaatgg
1381 ccagagcaaa ctgcaagaaa tttgcttttg ttcatatatc ttttgcacaa tttgaactgt
1441 cacaaggtaa tgtcaaaaaa agtaaacaac ttcttcaaaa agctgtagaa cgtggagcag
1501 taccactaga aatgctggaa attgccctgc ggaatttaaa cctccaaaaa agcagctgc
1561 tttcagagga ggaaaagaag aatttatcag catctacggt attaactgcc caagaatcat
1621 tttccggttc acttgggcat ttacagaata ggaacaacag ttgtgattcc agaggacaga
1681 ctactaaagc caggttttta tatggagaga acatgccacc acaagatgca gaaataggtt
1741 accggaattc attgagacaa actaacaaaa ctaaacagtc atgcccattt ggaagagtcc
1801 cagttaacct tctaaatagc ccagattgtg atgtgaagac agatgattca gttgtacctt
1861 gttttatgaa aagacaaacc tctagatcag aatgccgaga tttggttgtg cctggatcta
1921 aaccaagtgg aaatgattcc tgtgaattaa gaaatttaaa gtctgttcaa aatagtcatt
1981 tcaaggaacc tctggtgtca gatgaaaaga gttctgaact tattattact gattcaataa
2041 ccctgaagaa taaaacggaa tcaagtcttc tagctaaatt agaagaaact aaagagtatc
2101 aagaaccaga ggttccagag agtaaccaga acagtggcca agctaagaga aagtcagagt
2161 gtattaacca gaatcctgct gcatcttcaa atcactggca gattccggag ttagcccgaa
2221 aagttaatac agagcagaaa cataccactt ttgagcaacc tgtcttttca gtttcaaaac
2281 agtcaccacc aatatcaaca tctaaatggt ttgacccaaa atctatttgt aagacaccaa
2341 gcagcaatac cttggatgat tacatgagct gttttagaac tccagttgta aagaatgact
2401 ttccacctgc ttgtcagttg tcaacacctt atggccaacc tgcctgtttc cagcagcaac
2461 agcatcaaat acttgccact ccacttcaaa atttacaggt tttagcatct tcttcagcaa
2521 atgaatgcat ttcggttaaa ggaagaattt attccatatt aaagcagata ggaagtggag
2581 gttcaagcaa ggtatttcag gtgttaaatg aaaagaaaca gatatatgct ataaaatatg
2641 tgaacttaga agaagcagat aaccaaactc ttgatagtta ccggaacgaa atagcttatt
2701 tgaataaact acaacaacac agtgataaga tcatccgact ttatgattat gaaatcacgg
2761 accagtacat ctacatggta atggagtgtg gaaatattga tcttaatagt tggcttaaaa
2821 agaaaaaatc cattgatcca tgggaacgca gagttactg gaaaaatatg ttagaggcag
2881 ttcacacaat ccatcaacat ggcattgttc acagtgatct taaaccagct aactttctga
2941 tagttgatgg aatgctaaag ctaattgatt tgggattgc aaaccaaatg caaccagata
3001 caacaagtgt tgttaaagat tctcaggttg gcacagttaa ttatatgcca ccagaagcaa
3061 tcaaagatat gtcttcctcc agagagaatg ggaaatctaa gtcaaagata gccccaaaa
3121 gtgatgtttg gtccttagga tgtatttgt actatatgac ttacgggaaa acaccatttc
3181 agcagataat taatcagatt tctaaattac atgccataat tgatcctaat catgaaattg
3241 aatttcccga tattccagag aaagatcttc aagatgtgtt aaagtgttgt ttaaaagggg
```

FIG. 15A

```
3301 acccaaaaca gaggatatcc attcctgagc tcctggctca tccatatgtt caaattcaaa
3361 ctcatccagt taaccaaatg gccaagggaa ccactgaaga aatgaaatat gttctgggcc
3421 aacttgttgg tctgaattct cctaactcca ttttgaaagc tgctaaaact ttatatgaac
3481 actatagtgg tggtgaaagt cataattctt catcctccaa gactttttgaa aaaaaaaggg
3541 gaaaaaaatg atttgcagtt attcgtaatg tcagatagga ggtataaaat atattggact
3601 gttatactct tgaatccctg tggaaatcta catttgaaga caacatcact ctgaagtgtt
3661 atcagcaaaa aaaattcagt gagattatct ttaaaagaaa actgtaaaaa tagcaaccac
3721 ttatggcact gtatatattg tagacttgtt ttctctgttt tatgctcttg tgtaatctac
3781 ttgacatcat tttactcttg gaatagtggg tggatagcaa gtatattcta aaaaactttg
3841 taaataaagt tttgtggcta aaatga (SEQ ID NO: 1)
```

FIG. 15B

```
  1   mesedlsgre ltidsimnkv rdiknkfkne dltdelslnk isadttdnsg tvnqimmman
 61   npedwlslll kleknsvpls dallnkligr ysqaiealpp dkygqnesfa riqvrfaelk
121   aiqepddard yfqmaranck kfafvhisfa qfelsqgnvk kskqllqkav ergavpleml
181   eialrnlnlq kkqllseeek knlsastvlt aqesfsgslg hlqnrnnscd srgqttkarf
241   lygenmppqd aeigyrnslr qtnktkqscp fgrvpvnlln spdcdvktdd svvpcfmkrq
301   tsrsecrdlv vpgskpsgnd scelrnlksv qnshfkeplv sdeksselii tdsitlknkt
361   essllaklee tkeyqepevp esnqkqwqsk rksecinqnp aassnhwqip elarkvnteq
421   khttfeqpvf svskqsppis tskwfdpksi cktpssntld dymscfrtpv vkndfppacq
481   lstpygqpac fqqqqhqila tplqnlqvla sssanecisv kgriysilkq igsggsskvf
541   qvlnekkqiy aikyvnleea dnqtldsyrn eiaylnklqq hsdkiirlyd yeitdqyiym
601   vmecgnidln swlkkkksid pwerksywkn mleavhtihq hgivhsdlkp anflivdgml
661   klidfgianq mqpdttsvvk dsqvgtvnym ppeaikdmss srengksksk ispksdvwsl
721   gcilyymtyg ktpfqqiinq isklhaiidp nheiefpdip ekdlqdvlkc clkrdpkqri
781   sipellahpy vqiqthpvnq makgtteemk yvlgqlvgln spnsilkaak tlyehysgge
841   shnssssktf ekkrgkk (SEQ ID NO: 2)
```

FIG. 16

METHODS OF INHIBITING TUMOR GROWTH USING TTK ANTAGONISTS

RELATED APPLICATION

This application is the US National Stage of PCT Application No. PCT/CA2008/002228, filed Dec. 19, 2008, which published in English and designates the U.S. and claims priority to U.S. Provisional Application No., 61/008,649 filed Dec. 21, 2007. The entire teachings of these applications are incorporated herein by reference.

SEQUENCE LISTING

The instant application contains a Sequence Listing which has been submitted via EFS-Web and is hereby incorporated by reference in its entirety. Said ASCII copy, created on Aug. 25, 2010, is named SEQUENCE LISTING 098116-0105.txt.

BACKGROUND OF THE INVENTION

Cancer is the second leading cause of death after heart disease and is the primary cause of death in women between the ages of 35 and 74 in the United States. Based on estimates of the National Institutes of Health, overall costs for cancer in the year 2000 were 180.2 billion U.S. dollars. Cancer-related costs account for about 10 percent of the total amount spent on disease treatment in the United States. Thus, cancer is a major national burden.

Breast cancer is the most common cancer among American women, except for skin cancers. In addition, breast cancer is the second leading cause of cancer death in women, exceeded only by lung cancer. The chance of developing invasive breast cancer at some time in a woman's life is about 1 in 8 (12%). Women living in North America have the highest rate of breast cancer in the world and it is estimated that about 178,480 new cases of invasive breast cancer will be diagnosed among women in the United States in 2007.

Recent studies have led to the identification of classes, or sub-types, of breast cancer that are defined by gene expression profiles and molecular features (Lønning et al., *Endocrine-Related Cancer* 8:259-263 (2001)). These include Luminal A, Luminal B, HER2-type, normal breast-like and basal-like breast cancers. Basal-like breast cancers are high-grade cancers that are associated with rapid growth and poor prognosis, including high risk for metastasis, recurrence, and death. There is no definitive test or validated clinical assay at this time that accurately identifies basal-like breast cancers. Accordingly, there is an urgent need to identify new markers that can be used to recognize basal-like breast cancer more readily and to develop targeted treatments for this disease.

Human TTK protein kinase (TTK), also known as tyrosine threonine kinase, dual specificity protein kinase TTK, Monopolar Spindle 1 (Mps1) and Phosphotyrosine-Picked Threonine Kinase (PYT), is a conserved multispecific kinase that is capable of phosphorylating serine, threonine and tyrosine residues when expressed in *E. coli* (Mills et al., *J. Biol. Chem.* 22(5): 16000-16006 (1992)). TTK mRNA is not expressed in the majority of physiologically normal tissues in human (Id). TTK mRNA is expressed in some rapidly proliferating tissues, such as testis and thymus, as well as in some tumors (TTK mRNA was not expressed in renal cell carcinoma, was expressed in 50% of breast cancer samples, was expressed in testicular tumors and ovarian cancer samples) (Id). TTK is expressed in some cancer cell lines and tumors relative to normal counterparts (Id.; see also WO 02/068444 A1).

The yeast homolog of human TTK, Mps1, is required for normal cell cycle progression and has been shown to have a role in centrosome/spindle body duplication, the mitotic spindle checkpoint and cytokinesis (Winey and Huneycutt, *Oncogene* 21: 6161-6169 (2002)). Studies in *Drosophila* and vertebrates have confirmed that several of these functions are conserved in higher eukaryotes, including humans (Fisk and Winey, *Curr. Biol.* 14: R1058-1060 (2004); Fischer et al., *Curr. Biol.* 14: 2019-2024 (2004); Fisk et al., *PNAS* 100(25): 14875-14880 (2003)). The specific biochemical role of TTK in cellular physiology is not currently understood.

The requirement of normal TTK kinase activity for controlled cell cycle progression in yeast, *Drosophila*, and vertebrates, including humans, combined with the detection of TTK overexpression in some human cancer samples and cancer cell lines indicates that TTK should be investigated further as a potential target for therapeutic anti-cancer agents. However, the role of TTK in the pathology of breast cancer and particular subtypes of breast cancer is not understood.

There is a need to determine whether TTK expression and/or activity is associated with particular subtypes of breast cancer. In addition, there is a need to identify and develop therapeutic agents that target TTK expression and/or activity to treat breast cancer subtypes that are characterized by TTK overexpression.

SUMMARY OF THE INVENTION

The present invention relates to a method for treating UK positive non-luminal breast cancer (e.g., a basal-like breast cancer, a HER-2 positive breast cancer) in a mammalian subject. In the method of the invention, a therapeutically effective amount of a TTK antagonist is administered to the mammalian subject. The TTK positive non-luminal breast cancer can be a basal-like breast cancer or a HER-2 positive breast cancer, such as a HER-2 positive, estrogen receptor (ER) negative breast cancer. The UK antagonist inhibits the expression and/or activity of a TTK gene or gene product and can be, for example, an antibody, an antigen-binding fragment of an antibody, a small interfering ribonucleic acid (siRNA), a peptide, a peptidomimetic, an antisense oligonucleotide, or a small molecule. The TTK antagonist can be administered with one or more other therapeutic agents, including, but not limited to, a HER-2 antagonist, such as trastuzumab.

The invention also relates to a method for treating a TTK positive soft tissue sarcoma in a mammalian subject. The method comprises administering a therapeutically effective amount of a TTK antagonist to the mammalian subject. Examples of TTK positive soft-tissue sarcomas that can be treated include TTK positive fibrosarcomas, leiomyosarcomas, dedifferentiated liposarcomas, pleiomorphic liposarcomas, malignant fibrous histiocytomas, round cell sarcomas and synovial sarcomas. The TTK antagonist can be, for example, an antibody, an antigen-binding fragment of an antibody, a small interfering ribonucleic acid (siRNA), a peptide, a peptidomimetic, an antisense oligonucleotide, or a small molecule, and can be administered with one or more other therapeutic agents.

The invention also relates to a method of treating a TTK positive basal-like breast cancer tumor in a mammalian subject comprising administering a therapeutically effective amount of a TTK antagonist to the mammalian subject. The TTK antagonist can be, for example, an antibody, an antigen-binding fragment of an antibody, a small interfering ribonucleic acid (siRNA), a peptide, a peptidomimetic, an antisense oligonucleotide, or a small molecule, and can be administered with one or more other therapeutic agents. Examples of TTK positive basal-like breast cancer tumors that can be treated include TTK positive metastatic tumors and carcinomas.

The invention also provides a method of treating a TTK positive breast cancer that is also HER-2 positive and ER negative in a mammalian subject. The method comprises administering a therapeutically effective amount of a TTK antagonist to the mammalian subject. The UK antagonist can be, for example, an antibody, an antigen-binding fragment of an antibody, a small interfering ribonucleic acid (siRNA), a peptide, a peptidomimetic, an antisense oligonucleotide, or a small molecule, and can be administered with one or more other therapeutic agents, including, but not limited to, a HER-2 antagonist, such as trastuzumab.

The invention further relates to a composition comprising a TTK antagonist, a HER-2 antagonist and a physiologically acceptable carrier. The HER-2 antagonist can be, for example, trastuzumab.

The invention further relates to a method for identifying a candidate for an anti-cancer therapy using a TTK antagonist. The method comprises providing a suitable tumor sample obtained from a subject and assessing expression of TTK in the tumor sample. According to the invention, expression of TTK by the tumor, or increased expression of TTK by the tumor relative to a suitable control, indicates that the subject is a candidate for an anti-cancer therapy using a TTK antagonist.

The invention also encompasses a method of diagnosing a non-luminal breast cancer in a subject. The method comprises providing a suitable tumor sample from breast tissue of the subject and assessing expression of TTK in said tumor sample. Expression of TTK by the tumor, or increased expression of TTK by the tumor relative to a suitable control, indicates that the subject has a basal-like breast cancer.

The invention also relates to a method of determining the prognosis of a subject who has a cancer. The method comprises providing a suitable tumor sample from the subject and assessing expression of TTK in the tumor sample. According to the invention, expression of TTK by the tumor, or increased expression of UK by the tumor relative to a suitable control, indicates reduced patient survival, increased risk of metastases or increased risk of relapse.

The invention further provides a method for screening a breast cancer patient as an aid for selecting aggressive cancer therapy. The method comprises providing a suitable sample from a patient and determining TTK expression in the sample. According to the invention, increased TTK expression in the sample from the patient as compared with a suitable control indicates the patient is a candidate for aggressive cancer therapy.

BRIEF DESCRIPTION OF THE DRAWINGS

FIG. 2A is a graph depicting TTK RNA expression in several normal breast cell lines and breast cancer cell lines, as determined by quantitative polymerase chain reaction (QPCR). TTK RNA is overexpressed in several breast cancer cell lines.

FIG. 2B is a picture of a Western blot depicting increased expression of TTK protein in breast cancer cell lines relative to normal breast cell lines. Hs578T, MDA-MB-231, MDA-MB-435, and MDA-MB-468 are non-luminal breast cancer cell lines and BT-474, MDA-MB-330, MDA-MB-453 and HCC1419 are luminal breast cancer cell lines. β-actin levels serve as a loading control.

FIG. 8A illustrates an association (p=5.9E-4) between high TTK expression and increased risk of breast cancer relapse.

FIG. 11A is a graph illustrating a reduction in the number of colonies formed in soft agar by T-47D breast cancer cells treated with UK-targeting siRNAs (siRNA #2 (FIG. 11C), siRNA #3 (FIG. 11D), siRNA POOL (FIG. 11E)), relative to T-47D breast cancer cells treated with non-targeting control siRNA that targets firefly luciferase (siCONTROL) (FIG. 11B). Results are based on two independent experiments.

FIG. 11B-11E is a series of photographs depicting a reduction in the number and size of colonies formed in soft agar by T-47D breast cancer cells treated with TTK-targeting siRNAs (siRNA #2, siRNA #3, siRNA POOL), relative to T-47D breast cancer cells treated with non-targeting control siRNA that targets firefly luciferase (siCONTROL). A 40 nM concentration of siRNA was used in each transfection.

FIGS. 15A and 15B show the human TTK cDNA sequence (Genbank Accession No. M86699).

FIG. 16 shows the human UK protein sequence (Genbank Accession No. NP003309).

DETAILED DESCRIPTION OF THE INVENTION

Definitions

Figure 1:
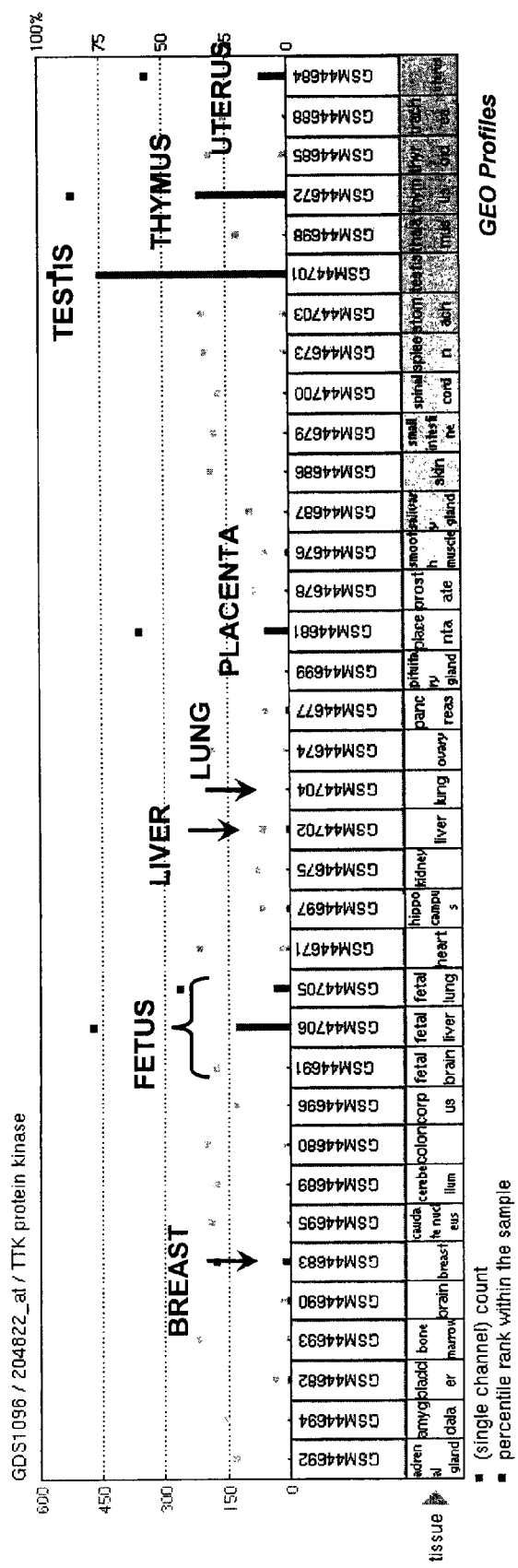
FIG. 1 is a microarray gene expression profile of 36 normal tissues illustrating that only certain physiologically normal tissues in human express TTK RNA.

As used herein, "TTK protein," "TTK kinase," or "TTK" refers to a naturally occurring or endogenous TTK (e.g., mammalian, human) protein, and to proteins having an amino acid sequence that is the same as that of naturally occurring or endogenous TTK protein (e.g., recombinant proteins, synthetic proteins). Accordingly "TTK protein," "TTK kinase," or "TTK" includes polymorphic or allelic variants and other isoforms of a TTK protein (e.g., mammalian, human) produced by, e.g., alternative splicing or other cellular processes, that occur naturally in mammals (e.g., humans, non-human primates). Preferably, the TTK protein is a human protein that has the amino acid sequence of SEQ ID NO: 2. (See, Genbank Accession No. NP003309 and FIG. 16).

As defined herein, a "TTK antagonist" is an agent (e.g., nucleic acid, protein, peptide, peptidomimetic, antibody, small molecule), which specifically and, preferably, selectively binds a TTK protein and inhibits (e.g., reduces, prevents) one or more activities of a TTK protein; or an agent that inhibits (e.g., reduces, prevents) the expression of a TTK gene and/or protein. A TTK antagonist can inhibit the activity of a TTK protein by, for example, inhibiting the binding of ATP, blocking the active site of the protein's kinase domain (e.g., amino acids 525-797 of SEQ ID NO:2) and/or blocking the association of TTK with one or more of its substrates (e.g., BLM helicase, CHK2/hCds1 protein kinase, Smad2, Smad3) in a cell. A TTK antagonist that inhibits the expression and/or activity of a TTK can be, for example, a natural or synthetic nucleic acid or nucleic acid analog, antisense molecule, small interfering RNA (siRNA), protein, peptide, antibody, small molecule, chemical compound or the like.

As used herein, the term "peptide", refers to a compound consisting of from about 2 to about 100 amino acid residues wherein the amino group of one amino acid is linked to the carboxyl group of another amino acid by a peptide bond. Such peptides are typically less than about 100 amino acid residues in length and preferably are about 10, about 20, about 30, about 40 or about 50 residues. As used herein, the term "peptidomimetic", refers to molecules which are not polypeptides, but which mimic aspects of their structures. Peptidomimetic antagonists can be prepared by conventional chemical methods (see e.g., Damewood J. R. "Peptide Mimetic Design with the Aid of Computational Chemistry" in *Reviews in Computational Biology*, 2007, Vol. 9, pp. 1-80, John Wiley and Sons, Inc., New York, 1996; Kazmierski W. K., "*Methods of Molecular Medicine: Peptidomimetic Protocols*," Humana Press, New Jersey, 1999).

As defined herein, "therapy" is the administration of a particular therapeutic or prophalytic agent to a subject (e.g., a mammal, a human).

As defined herein a "treatment regimen" is a regimen in which one or more therapeutic or prophalytic agents are administered to a mammalian subject at a particular dose (e.g., level, amount, quantity) and on a particular schedule or at particular intervals (e.g., minutes, days, weeks, months).

As defined herein, "direct inhibition of tumor growth" refers to inhibited tumor growth (e.g., reduced tumor cell proliferation, tumor cell death) caused by the interaction of a therapeutic agent with a target in or on a tumor cell. Thus, a TTK antagonist can directly inhibit tumor growth by binding a TTK protein expressed by the cells of the tumor and inhibiting the activity of the TTK protein, for example. In addition, a TTK antagonist can directly inhibit tumor growth by inhibiting expression (e.g., decreasing nucleic acid (e.g., RNA) and/or protein) of a TTK gene product or protein in the cells of the tumor.

As defined herein, a "therapeutically effective amount" is an amount sufficient to achieve the desired therapeutic or prophylactic effect under the conditions of administration, such as an amount sufficient to inhibit (i.e., reduce, prevent) tumor cell growth (proliferation, size) and/or tumor progression (invasion, metastasis) for a particular cancer. The effectiveness of a therapy (e.g., the reduction/elimination of a tumor and/or prevention tumor growth) can be determined by suitable methods (e.g., in situ immunohistochemistry, imaging (MRI, NMR), $^3$H-thymidine incorporation).

As defined herein, an "anti-tumor effective amount" is an amount sufficient to directly inhibit tumor cell growth (e.g., proliferation) or survival.

As defined herein, an "anti-angiogenic effective amount" is an amount sufficient to inhibit angiogenesis.

As used herein, "aggressive therapy" is the administration of a therapeutic agent or agents at higher doses, more frequent doses, or a combination thereof, than is normally administered in a typical therapeutic regime. Aggressive therapy can also be the administration of a combination of therapeutic agents that are not typically administered in the same therapeutic regime. Aggressive therapy is often at or near the limit of tolerance for a subject receiving such therapy. For example, aggressive chemotherapy is sufficiently toxic that the subject's bone marrow is likely to fail (e.g., the bone marrow will no longer be able to produce hematopoeitic cells after aggressive therapy). To get around this anticipated side effect of aggressive therapy, the subject may receive an autologous bone marrow transplant, or receive a tissue-type matched bone marrow transplant.

As described herein, TTK expression or overexpression is associated with certain types of cancers, in particular non-luminal breast cancer subtypes, as well as soft-tissue sarcomas. In particular, the inventor have determined that TTK gene products (e.g., mRNA, protein) are expressed at higher levels in particular breast cancer subtypes, such as basal-like breast cancer and HER-2 positive/estrogen receptor negative breast cancer, relative to normal breast cells or tissues. In addition, the inventor have shown that antagonists of TTK can directly inhibit proliferation (e.g., by inducing apoptosis, by inducing cell cycle arrest, by inhibiting anchorage-independent cell growth) of cancer cells that express TTK. Thus, antagonists of TTK can be used to treat cancers, for example, by inhibiting tumor growth and/or progression (e.g., in cancer patients). Accordingly, the invention provides a method for the targeted treatment of a cancer (e.g., a non-luminal breast cancer, a basal-like breast cancer tumor, a HER-2 positive and ER-negative breast cancer tumor, a soft tissue sarcoma) that expresses TTK and, further, provides for a pharmaceutical composition comprising a TTK antagonist. The invention also provides a method of treating a non-luminal subtype breast cancer by administering a TTK antagonist alone or in combination with one or more other therapeutic agents (e.g., a HER-2 antagonist).

Inhibition of the expression or activity of a TTK protein provides an effective and selective mechanism by which to treat cancers (e.g., tumors) that express TTK. Thus, one aspect of the present invention relates to a method for treating cancer in a mammalian subject comprising administering to the subject a therapeutically effective amount of a TTK antagonist.

TTK Antagonists

The TTK antagonist can be an antibody or antigen-binding fragment thereof that selectively binds a TTK protein. The term "antibody" is intended to encompass all types of polyclonal and monoclonal antibodies (e.g., human, chimeric, humanized, primatized, veneered, single chain, domain antibodies (dAbs)) and antigen-binding fragments of antibodies (e.g., Fv, Fc, Fd, Fab, Fab', F(ab'), dAb). (See e.g., Harlow et al., Antibodies A Laboratory Manual, Cold Spring Harbor Laboratory, 1988). In a particular embodiment, the UK-specific antibody is a human antibody or humanized antibody. TTK-specific antibodies can also be directly or indirectly linked to a cytotoxic agent.

Several antibodies that selectively bind TTK have been produced and are commercially available (e.g., from Abgent, Abnova Corporation, ABR-Affinity BioReagents, Bethyl laboratories, Cell Signaling Technology, GeneTex, Lifespan Biosciences, Novus Biologicals, Proteintech Group, Inc., Santa Cruz Biotechnology, Inc.). In addition, antibodies that selectively bind to and inhibit the activity of a TTK protein include monoclonal antibodies N1, N2 and C1 described in Stucke et al., EMBO J. 21(7):1723-1732 (2002).

Other antibodies or antibody fragments which selectively bind to and inhibit the activity of a TTK protein can also be produced, constructed, engineered and/or isolated by conventional methods or other suitable techniques. For example, antibodies which are specific for a TTK protein can be raised against an appropriate immunogen, such as a recombinant mammalian (e.g., human) TTK protein or portion thereof (including synthetic molecules, e.g., synthetic peptides). A variety of methods have been described (see e.g., Kohler et al., Nature, 256: 495-497 (1975) and Eur. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Antibodies can also be raised by immunizing a suitable host (e.g., mouse) with cells that express TTK (e.g., cancer cells/cell lines) or cells engineered to express UK (e.g., transfected cells). (See e.g., Chuntharapai et al., J. Immunol., 152:1783-1789 (1994); Chuntharapai et al. U.S. Pat. No. 5,440,021). For the production of monoclonal antibodies, a hybridoma can be produced by fusing a suitable immortal cell line (e.g., a myeloma cell line such as SP2/0 or P3X63Ag8.653) with antibody producing cells. The antibody producing cells can be obtained from the peripheral blood, or preferably, the spleen or lymph nodes, of humans or other suitable animals immunized with the antigen of interest. The fused cells (hybridomas) can be isolated using selective culture conditions, and cloned by limited dilution. Cells which produce antibodies with the desired specificity can be selected by a suitable assay (e.g., ELISA).

Antibody fragments can be produced by enzymatic cleavage or by recombinant techniques. For example, papain or pepsin cleavage can generate Fab or F(ab')$_2$ fragments, respectively. Other proteases with the requisite substrate specificity can also be used to generate Fab or F(ab')$_2$ fragments. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain. Single chain antibodies, and human, chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194, 276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. In one embodiment, cloned variable regions (e.g., dAbs) can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

Other suitable methods of producing or isolating antibodies of the requisite specificity can be used, including, for example, methods which select a recombinant antibody or antibody-binding fragment (e.g., dAbs) from a library (e.g., a phage display library), or which rely upon immunization of transgenic animals (e.g., mice). Transgenic animals capable of producing a repertoire of human antibodies are well-known in the art (e.g., Xenomouse® (Abgenix, Fremont, Calif.)) and can be produced using suitable methods (see e.g., Jakobovits et al., *Proc. Natl. Acad. Sci. USA*, 90: 2551-2555 (1993); Jakobovits et al., *Nature*, 362: 255-258 (1993); Lonberg et al., U.S. Pat. No. 5,545,806; Surani et al., U.S. Pat. No. 5,545,807; Lonberg et al., WO 97/13852).

A TTK antagonist can be a peptide (e.g., synthetic, recombinant, fusion or derivatized) that specifically binds to, and inhibits (reduces, prevents, decreases) the activity of, the TTK protein. The peptide can be linear, branched or cyclic, e.g., a peptide having a heteroatom ring structure that includes several amide bonds. In a particular embodiment, the peptide is a cyclic peptide.

Peptides, including cyclic peptides, that are selective for binding to a particular domain (e.g., unique domain) of a TTK protein can be produced. A peptide can be, for example, derived or removed from a native protein by enzymatic or chemical cleavage, or can be synthesized by suitable methods, for example, solid phase peptide synthesis (e.g., Merrifield-type synthesis) (see, e.g., Bodanszky et al. "*Peptide Synthesis*," John Wiley & Sons, Second Edition, 1976). Peptides that are TTK antagonists can also be produced, for example, using recombinant DNA methodologies or other suitable methods (see, e.g., Sambrook J. and Russell D. W., *Molecular Cloning: A Laboratory Manual*, $3^{rd}$ Edition, Cold Spring Harbor Laboratory Press, Cold Spring Harbor, N.Y., 2001). TTK antagonists can also be fusion peptides fused, for example to a carrier protein (e.g., myc, his, glutathione sulfhydryl transferase) and/or tagged (e.g., radiolabeled, fluorescently labeled).

A peptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitruline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are disclosed in, for example, Green and Wuts, "*Protecting Groups in Organic Synthesis*", John Wiley and Sons, 1991. The functional groups of a peptide can also be derivatized (e.g., alkylated) using art-known methods.

Peptides can be synthesized and assembled into libraries comprising a few to many discrete molecular species. Such libraries can be prepared using methods of combinatorial chemistry, and can be screened using any suitable method to determine if the library comprises peptides with a desired biological activity. Such peptide antagonists can then be isolated using suitable methods.

The peptide can comprise modifications (e.g., amino acid linkers, acylation, acetylation, amidation, methylation, terminal modifiers (e.g., cyclizing modifications)), if desired. The peptide can also contain chemical modifications (e.g., N-methyl-α-amino group substitution). In addition, the peptide antagonist can be an analog of a known and/or naturally-occurring peptide, for example, a peptide analog having conservative amino acid residue substitution(s). These modifications can improve various properties of the peptide (e.g., solubility, binding), including its TTK antagonist activity.

Peptidomimetics can be prepared that are TTK antagonists. For example, polysaccharides can be prepared that have the same functional groups as peptides. Peptidomimetics can be designed, for example, by establishing the three dimensional structure of a peptide agent in the environment in which it is bound or will bind to a target molecule. The peptidomimetic comprises at least two components, the binding moiety or moieties and the backbone or supporting structure.

The binding moieties are the chemical atoms or groups which will react or form a complex (e.g., through hydrophobic or ionic interactions) with a target molecule, for example, with the amino acid(s) at or near the active site of the kinase. For example, the binding moieties in a peptidomimetic can be the same as those in a peptide or protein antagonist. The binding moieties can be an atom or chemical group which reacts with the receptor in the same or similar manner as the binding moiety in the peptide antagonist. For example, computational chemistry can be used to design peptide mimetics of the ATP-binding site and/or active site of the TTK protein, for instance. Examples of binding moieties suitable for use in designing a peptidomimetic for a basic amino acid in a peptide include nitrogen containing groups, such as amines, ammoniums, guanidines and amides or phosphoniums. Examples of binding moieties suitable for use in designing a peptidomimetic for an acidic amino acid include, for example, carboxyl, lower alkyl carboxylic acid ester, sulfonic acid, a lower alkyl sulfonic acid ester or a phosphorous acid or ester thereof.

The supporting structure is the chemical entity that, when bound to the binding moiety or moieties, provides the three dimensional configuration of the peptidomimetic. The supporting structure can be organic or inorganic. Examples of organic supporting structures include polysaccharides, polymers or oligomers of organic synthetic polymers (such as, polyvinyl alcohol or polylactide). It is preferred that the supporting structure possess substantially the same size and dimensions as the peptide backbone or supporting structure. This can be determined by calculating or measuring the size of the atoms and bonds of the peptide and peptidomimetic. In one embodiment, the nitrogen of the peptide bond can be substituted with oxygen or sulfur, for example, forming a polyester backbone. In another embodiment, the carbonyl can be substituted with a sulfonyl group or sulfinyl group, thereby forming a polyamide (e.g., a polysulfonamide). Reverse amides of the peptide can be made (e.g., substituting one or more -CONH- groups for a -NHCO- group). In yet another embodiment, the peptide backbone can be substituted with a polysilane backbone.

These compounds can be manufactured by known methods. For example, a polyester peptidomimetic can be prepared by substituting a hydroxyl group for the corresponding α-amino group on amino acids, thereby preparing a hydroxyacid and sequentially esterifying the hydroxyacids, optionally blocking the basic and acidic side chains to minimize side reactions. Determining an appropriate chemical synthesis route can generally be readily identified upon determining the chemical structure.

Peptidomimetics can be synthesized and assembled into libraries comprising a few to many discrete molecular species. Such libraries can be prepared using well-known methods of combinatorial chemistry, and can be screened to determine if the library comprises one or more peptidomimetics which have the desired activity. Such peptidomimetic antagonists can then be isolated by suitable methods.

TTK antagonists can also be small molecules. Examples of small molecules include organic compounds, organometallic compounds, inorganic compounds, and salts of organic, organometallic or inorganic compounds. Atoms in a small molecule are typically linked together via covalent and/or ionic bonds. The arrangement of atoms in a small organic molecule may represent a chain (e.g. a carbon-carbon chain or a carbon-heteroatom chain), or may represent a ring containing carbon atoms, e.g. benzene or a policyclic system, or a combination of carbon and heteroatoms, i.e., heterocycles such as a pyrimidine or quinazoline. Although small molecules can have any molecular weight, they generally include molecules that are less than about 5,000 daltons. For example, such small molecules can be less than about 1000 daltons and, preferably, are less than about 750 daltons or, more preferably, are less than about 500 daltons. Small molecules and other non-peptidic TTK antagonists can be found in nature (e.g., identified, isolated, purified) and/or produced synthetically (e.g., by traditional organic synthesis, bio-mediated synthesis, or a combination thereof). See e.g. Ganesan, Drug Discov. Today 7(1): 47-55 (January 2002); Lou, Drug Discov. Today, 6(24): 1288-1294 (December 2001). Examples of naturally occurring small molecules include, but are not limited to, hormones, neurotransmitters, nucleotides, amino acids, sugars, lipids, and their derivatives.

Figure 13A:
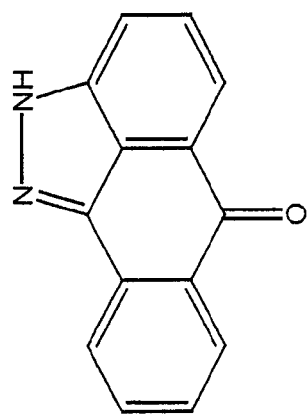
FIG. 13A-13C depicts the chemical structures of SP6000125 (FIG. 13A) and particular substituted derivatives of SP600125 (FIG. 13B-13C).
Figure 13B:
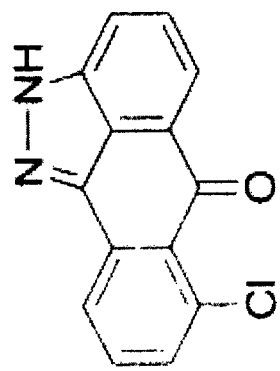
Figure 13C:
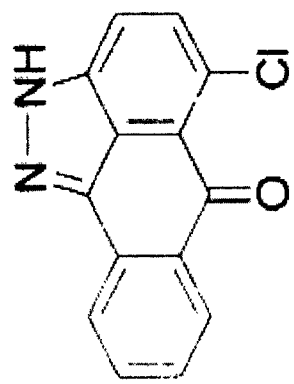
Figure 14A:
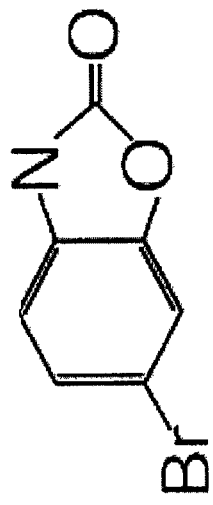
FIG. 14A-14C depicts the chemical structures of cincreasin (FIG. 14A) and particular cincreasin derivatives (FIG. 14B-14C).
Figure 14B:
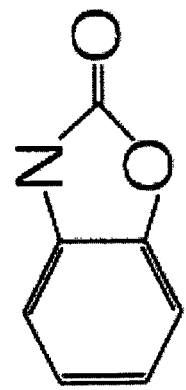
Figure 14C:
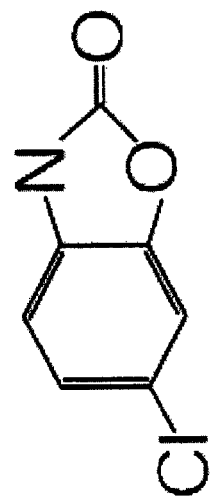

A small molecule TTK antagonist according to the present invention, and physiologically acceptable salts thereof, can inhibit the kinase activity of TTK (e.g., by directly competing with ATP for binding to the ATP-binding pocket of TTK). Suitable small molecule TTK antagonists for use in the methods of the invention include, for example, anthrapyrazolone compounds and physiologically acceptable salts thereof. Examples of specific anthrapyrazolone compounds useful in the methods of the invention include anthra(1,9-cd)pyrazol-6(2H)-one 1,9-pyrazoloanthrone (SP600125) (FIG. 13A), which is a reversible ATP-competitive inhibitor UK and Jun N-terminal family kinases (JNK), and particular substituted derivatives of SP600125 (see, for example, FIG. 13B-13C) (Bennett et al., *PNAS* 98(24):13681-13686 (2001); Schmidt et al., *EMBO Reports* 6(9): 866-872 (2005)). SP600125 is available commercially (A.G. Scientific, Inc.; Sigma-Aldrich; Biomol International, LP; SuperArray Bioscience Corporation). Other examples of small molecule TTK antagonists include cincreasin (FIG. 14A) and related compounds, such as isocyanate and halogen-substituted derivatives (see, for example, FIG. 14B-14C) of cincreasin (Dorer et al., *Curr. Biol.* 15:1070-1076 (2005)).

Agents having TTK binding specificity, including small molecules, can be identified in a screen, for example, a high-throughput screen of chemical compounds and/or libraries (e.g., chemical, peptide, nucleic acid libraries). Compounds or small molecules can be identified from numerous available libraries of chemical compounds from, for example, the Chemical Repository of the National Cancer Institute and the Molecular Libraries Small Molecules Repository (PubChem), as well as libraries of the Institute of Chemistry and Cell Biology at Harvard University and other libraries that are available from commercial sources (e.g., Chembridge, Peakdale, CEREP, MayBridge, Bionet). Such libraries or collections of molecules can also be prepared using well-known chemical methods, such as well-known methods of combinatorial chemistry. The libraries can be screed to identify compounds that bind and inhibit TTK. Identified compounds can serve as lead compounds for further diversification using well-known methods of medicinal chemistry. For example, a collection of compounds that are structural variants of the lead can be prepared and screened for TTK binding and/or inhibitory activity. This can result in the development of a structure activity relationship that links the structure of the compounds to biological activity. Compounds that have suitable binding and inhibitory activity can be developed further for in vivo use.

Agents that bind TTK can be evaluated further for TTK antagonist activity. For example, a composition comprising a TTK protein can be used in a screen or binding assay to detect and/or identify agents that bind and antagonize the TTK protein. Compositions suitable for use include, for example, cells that naturally express a TTK protein (e.g., one or more non-luminal breast cancer cell line described herein), extracts of such cells, and recombinant TTK protein.

An agent that binds a TTK protein can be identified in a competitive binding assay, for example, in which the ability of a test agent to inhibit the binding of TTK to a reference agent is assessed. The reference agent can be a substrate, such as ATP, an endogenous substrate (e.g., BLM helicase, CHK2/hCds1 protein kinase, Smad2, Smad3), or an exogenous substrate (e.g., myelin basic protein) that is phosphorylated by UK. Suitable endogenous substrates for TTK include BLM helicase, CHK2/hCds1 protein kinase, Smad2 and Smad3. The reference agent can be labeled with a suitable label (e.g., radioisotope, epitope label, affinity label (e.g., biotin and avidin or streptavadin), spin label, enzyme, fluorescent group, chemiluminescent group, dye, metal (e.g., gold, silver), magnetic bead) and the amount of labeled reference agent required to saturate the TTK protein in the assay can be determined. The specificity of the formation of the complex between the TTK protein and the test agent can be determined using a suitable control (e.g., unlabeled agent, label alone).

The capacity of a test agent to inhibit formation of a complex between the reference agent and a TTK protein can be determined as the concentration of test agent required for 50% inhibition ($IC_{50}$ value) of specific binding of labeled reference agent. Specific binding is preferably defined as the total binding (e.g., total label in complex) minus the non-specific binding. Non-specific binding is preferably defined as the amount of label still detected in complexes formed in the presence of excess unlabeled reference agent. Reference agents suitable for use in the method include molecules and compounds which specifically bind to TTK, e.g., an endogenous or exogenous substrate or an antibody specific for UK (e.g., sc-540, Santa Cruz Biotechnology).

An agent that antagonizes a TTK protein can be identified by screening for agents that have an ability to antagonize (reduce, prevent, inhibit) one or more activities of TTK, such as, for example, a binding activity (e.g., the binding of TTK to a substrate) or a kinase activity (e.g., the phosphorylation of a substrate by TTK). Such activities can be assessed using an appropriate in vitro or in vivo assay. Exemplary in vitro kinase assays for TTK activity have been described previously (Stucke et al., *EMBO J.* 21(7):1723-1732 (2002); Wei et al., *J. Biol. Chem.* 280(9): 7748-7757 (2005)). For example, UK protein (e.g., endogenous TTK protein that is present in, or isolated from, a human cell extract, recombinant TTK protein) is washed three times in TTK kinase buffer [50 mM Tris-HCl pH 7.5, 10 mM $MgCl_2$, 0.5 mM dithiothreitol (DTT), 10 mM β-glycerophosphate, 100 μM $Na_3VO_4$]. Kinase reactions are carried out for 30 min at 30° C. in UK kinase buffer supplemented with 10 μM ATP, 2 μCi of [$\gamma^{32}P$] ATP (Amersham) and 0.5 mg/ml of myelin basic protein (MBP) as a substrate. Reactions are stopped by addition of gel sample buffer and heating at 95° C. for 5 min. Proteins are then resolved by SDS-PAGE and $^{32}P$ incorporation is visualized by autoradiography. A particularly suitable high-throughput ELISA based assay has also been described (CycLex® Human Mps1/TTK kinase Assay/Inhibitor Screening Kit, Catalog #CY-1179, CycLex Co., Ltd., Nagano, Japan). Exemplary assays for assessing TTK kinase activity in vivo also have been described (See, for example, Leng et al., *PNAS* 103(31):11485-11490 (2006); Zhu et al., *J. Biol. Chem.* 282 (25): 18327-18338 (2007)).

The ability of an agent that binds a TTK protein to antagonize one or more activities of TTK can also be assessed by measuring one or more of the TTK-mediated activities. Such TTK-mediated activities include inhibition of cell death of cancer cells, inhibition of cell cycle arrest of cancer cells and anchorage-dependent cell growth in vitro. Thus, assays for detecting these TTK-mediated activities can be used to evaluate the antagonist activity of a test agent (e.g., the ability of a test agent to inhibit one or more activities of TTK). Suitable assays include standard cell proliferation assays (e.g., BrdU incorporation, $^3$H-thymidine incorporation; See e.g., Friedlander M. et al. *Science* 270:1500-1502, 1995; Klemke R. L., *J. Cell. Biol.* 131:791-805, 1995; Kerr J. S. et al., *Anticancer Res.* 19:959-968, 1999), as well as the SRB cell viability assay, the flow cytometry assay and the colony formation assay described herein (See Exemplification under Materials and Methods and Example 3).

Once a TTK antagonist is identified, the ability of the TTK antagonist to interefere with (e.g., reduce, inhibit, prevent) one or more biological functions or properties associated with TTK kinase activity in a cell can be assessed, for example, using a cell-based assay designed to measure a particular biological function or property associated with TTK. Such biological functions and properties that are known to be associated with TTK expression and/or activity include, but are not limited to, centrosome duplication, mitotic checkpoint arrest, and localization to kinetocohores (Winey and Huneycutt, *Oncogene* 21: 6161-6169 (2002)); Stucke et al., *EMBO J.* 21(7): 1723-1732 (2002); Fisk et al., *PNAS* 100(25): 14875-14880 (2003)).

TTK antagonists are also agents that inhibit (reduce, decrease, prevent) the expression of a TTK protein. Agents (small molecules, peptides, nucleic acids, oligonucleotides) that inhibit TTK gene expression (e.g., transcription, mRNA processing, translation) are effective TTK antagonists. For example, small interfering ribonucleic acids (siRNAs) and, similarly, short hairpin ribonucleic acids (shRNAs) which are processed into short siRNA-like molecules in a cell, can prevent the expression (translation) of the TTK protein. siRNA molecules can be polynucleotides that are generally about 20 to about 25 nucleotides long and are designed to bind specific RNA sequence (e.g., TTK mRNA). siRNAs silence gene expression in a sequence-specific manner, binding to a target RNA (e.g., an RNA having the complementary sequence) and causing the RNA to be degraded by endoribonucleases. siRNA molecules able to inhibit the expression of the TTK gene product can be produced by suitable methods. There are several algorithms that can be used to design siRNA molecules that bind the sequence of a gene of interest (see e.g., Mateeva O. et al. *Nucleic Acids Res.* 35(8):Epub, 2007; Huesken D. et al., *Nat. Biotechnol.* 23:995-1001; Jagla B. et al., *RNA* 11:864-872, 2005; Shabalinea S. A. *BMC Bioinformatics* 7:65, 2005; Vert J. P. et al. *BMC Bioinformatics* 7:520, 2006). Expression vectors that can stably express siRNA or shRNA are available. (See e.g., Brummelkamp, T. R., *Science* 296: 550-553, 2002, Lee, N S, et al., *Nature Biotechnol.* 20:500-505, 2002; Miyagishi, M., and Taira, K. *Nature Biotechnol.* 20:497-500, 2002; Paddison, P. J., et al., *Genes & Dev.* 16:948-958, 2002; Paul, C. P., et al., *Nature Biotechnol.* 20:505-508; 2002; Sui, G., et al., *Proc. Natl. Acad. Sci. USA* 99(6):5515-5520, 2002; Yu, J-Y, et al., *Proc. Natl. Acad. Sci. USA* 99(9):6047-6052, 2002; Elbashir, S M, et al., *Nature* 411:494-498, 2001.). Stable expression of siRNA/shRNA molecules is advantageous in the treatment of cancer as it enables long-term expression of the molecules, potentially reducing and/or eliminating the need for repeated treatments.

Antisense oligonucleotides (e.g., DNA, riboprobes) can also be used as TTK antagonists to inhibit TTK expression. Antisense oligonucleotides are generally short (~13 to ~25 nucleotides) single-stranded nucleic acids which specifically hybridize to a target nucleic acid sequence (e.g., mRNA) and induce the degradation of the target nucleic acid (e.g., degradation of the RNA through RNase H-dependent mechanisms) or sterically hinder the progression of splicing or translational machinery. (See e.g., Dias N. and Stein C. A., *Mol. Can. Ther.* 1:347-355, 2002). There are a number of different types of antisense oligonucleotides that can be used as TTK antagonists including methylphosphonate oligonucleotides, phosphorothioate oligonucleotides, oligonucleotides having a hydrogen at the 2'-position of ribose replaced by an O-alkyl group (e.g., a methyl), polyamide nucleic acid (PNA), phosphorodiamidate morpholino oligomers (deoxyribose moiety is replaced by a morpholine ring), PN (N3'→P5' replacement of the oxygen at the 3' position on ribose by an amine group) and chimeric oligonucleotides (e.g., 2'-O-Methyl/phosphorothioate). Antisense oligonucleotides can be designed to be specific for a protein using predictive algorithms. (See e.g., Ding, Y., and Lawrence, C. E., *Nucleic Acids Res.*, 29:1034-1046, 2001; Sczakiel, G., *Front. Biosci.*, 5:D194-D201, 2000; Scherr, M., et al., *Nucleic Acids Res.*, 28:2455-2461, 2000; Patzel, V., et al. *Nucleic Acids Res.*, 27:4328-4334, 1999; Chiang, M. Y., et al., *J. Biol. Chem.*, 266:18162-18171, 1991; Stull, R. A., et al., *Nucleic Acids Res.*, 20:3501-3508, 1992; Ding, Y., and Lawrence, C. E., *Comput. Chem.*, 23:387-400, 1999; Lloyd, B. H., et al., *Nucleic Acids Res.*, 29:3664-3673, 2001; Mir, K. U., and Southern, E. M., *Nat. Biotechnol.*, 17:788-792, 1999; Sohail, M., et al., *Nucleic Acids Res.*, 29:2041-2051, 2001; Altman, R. K., et al., *J. Comb. Chem.*, 1:493-508, 1999). The antisense oligonucleotides can be produced by suitable methods; for example, nucleic acid (e.g., DNA, RNA, PNA) synthesis using an automated nucleic acid synthesizer (from, e.g., Applied Biosystems) (see also Martin, P., *Helv. Chim. Acta* 78:486-504, 1995). Antisense oligonucleotides can also be stably expressed in a cell containing an appropriate expression vector.

Antisense oligonucleotides can be taken up by target cells (e.g., tumor cells) via the process of adsorptive endocytosis. Thus, in the treatment of a subject (e.g., mammalian), antisense TTK oligonucleotides can be delivered to target cells (e.g., tumor cells) by, for example, injection or infusion. For instance, purified oligonucleotides or siRNA/shRNA, can be administered alone or in a formulation with a suitable drug delivery vehicle (e.g., liposomes, cationic polymers, (e.g., poly-L-lysine' PAMAM dendrimers, polyalkylcyanoacrylate nanoparticles and polyethyleneimine) or coupled to a suitable carrier peptide (e.g., homeotic transcription factor, the Antennapedia peptide, Tat protein of HIV-1, E5CA peptide).

Ribozymes can also be used as TTK antagonists to inhibit TTK expression. Ribozymes are RNA molecules possessing enzymatic activity. One class of ribozymes is capable of repeatedly cleaving other separate RNA molecules into two or more pieces in a nucleotide base sequence specific manner. See Kim et al., *Proc Natl Acad Sci USA*, 84:8788 (1987); Haseloff & Gerlach, *Nature*, 334:585 (1988); and Jefferies et al., *Nucleic Acid Res*, 17:1371 (1989). Such ribozymes typically have two functional domains: a catalytic domain and a binding sequence that guides the binding of ribozymes to a target RNA through complementary base-pairing. Once a specifically-designed ribozyme is bound to a target mRNA, it enzymatically cleaves the target mRNA, typically reducing its stability and destroying its ability to directly translate an encoded protein. After a ribozyme has cleaved its RNA target, it is released from that target RNA and thereafter can bind and cleave another target. That is, a single ribozyme molecule can repeatedly bind and cleave new targets.

In accordance with the present invention, a ribozyme may target any portion of the mRNA encoding TTK. Methods for selecting a ribozyme target sequence and designing and making ribozymes are generally known in the art. See e.g., U.S. Pat. Nos. 4,987,071; 5,496,698; 5,525,468; 5,631,359; 5,646,020; 5,672,511; and 6,140,491, each of which is incorporated herein by reference in its entirety. For example, suitable ribozymes may be designed in various configurations such as hammerhead motifs, hairpin motifs, hepatitis delta virus motifs, group I intron motifs, or RNase P RNA motifs. See e.g., U.S. Pat. Nos. 4,987,071; 5,496,698; 5,525,468; 5,631,359; 5,646,020; 5,672,511; and 6,140,491; Rossi et al., *AIDS Res Human Retroviruses* 8:183 (1992); Hampel & Tritz, *Biochemistry* 28:4929 (1989); Hampel et al., *Nucleic Acids Res,* 18:299 (1990); Perrotta & Been, *Biochemistry* 31:16 (1992); and Guerrier-Takada et al., *Cell,* 35:849 (1983).

Ribozymes can be synthesized by the same methods used for normal RNA synthesis. For example, suitable methods are disclosed in Usman et al., *J Am Chem Soc,* 109:7845-7854 (1987) and Scaringe et al., *Nucleic Acids Res,* 18:5433-5441 (1990). Modified ribozymes may be synthesized by the methods disclosed in, e.g., U.S. Pat. No. 5,652,094; International Publication Nos. WO 91/03162; WO 92/07065 and WO 93/15187; European Patent Application No. 92110298.4; Perrault et al., *Nature,* 344:565 (1990); Pieken et al., *Science,* 253:314 (1991); and Usman & Cedergren, *Trends Biochem Sci,* 17:334 (1992).

Methods of Therapy

Using the methods of the invention, cancer can be treated by inhibiting tumor growth (e.g., directly inhibited) using a TTK antagonist (e.g., antibodies, siRNA molecules, small organic molecules, antisense oligonucleotides, chemical compounds, peptides, peptide mimetics).

Accordingly, one aspect of the invention relates to a method for treating a TTK positive non-luminal breast cancer in a mammalian subject comprising administering to the subject a therapeutically effective amount of a TTK antagonist. The non-luminal breast cancer (e.g., non-luminal breast cancer tumor) can be any estrogen-receptor (ER)-negative breast cancer (e.g., a HER-2 positive breast cancer, a basal-like breast cancer) that expresses TTK. In a particular embodiment, the non-luminal breast cancer treated is a HER-2 positive non-luminal breast cancer. In a more particular embodiment, a TTK positive basal-like breast cancer (e.g., a TTK positive basal-like breast cancer tumor) is treated by administering a TTK antagonist.

In another aspect, the invention relates to a method for treating a TTK positive soft tissue sarcoma (e.g., malignant tumor) in a mammalian subject comprising administering to the subject a therapeutically effective amount of a TTK antagonist. The soft tissue sarcoma can be derived from any soft tissue, such as a soft tissue that connects, supports, or surrounds various structures and organs of the body, including, but not limited to, smooth muscle, skeletal muscle, tendons, fibrous tissues, fatty tissue, blood and lymph vessels, perivascular tissue, nerves, mesenchymal cells and synovial tissues. In a particular embodiment, the soft tissue sarcoma is a fibrosarcoma, a gastrointestinal sarcoma, a leiomyosarcoma, a dedifferentiated liposarcoma, a pleimoprhic liposarcoma, a malignant fibrous histiocytoma, a round cell sarcoma, or a synovial sarcoma.

In a particular aspect of the method, a TTK antagonist inhibits tumor growth directly by inducing the death (e.g., apoptosis) of the cells of the tumor or by inhibiting the growth (e.g., proliferation) of the cells of the tumor.

A therapeutically effective amount of the TTK antagonist is administered in the methods of the invention. In one aspect, an "anti-tumor effective amount" of a TTK antagonist is administered to a patient in need thereof. For example, agents which directly inhibit tumor growth (e.g., chemotherapeutic agents) are conventionally administered at a particular dosing schedule and level to achieve the most effective therapy (e.g., to best kill tumor cells). Generally, about the maximum tolerated dose is administered during a relatively short treatment period (e.g., one to several days), which is followed by an off-therapy period. In a particular example, the chemotherapeutic cyclophosphamide is administered at a maximum tolerated dose of 150 mg/kg every other day for three doses, with a second cycle given 21 days after the first cycle. (Browder et al. *Can Res* 60:1878-1886, 2000). Similarly, the anti-HER-2 monoclonal antibody, trastuzumab, is administered to HER-2 positive breast cancer patients in one larger initial dose (4 mg/kg) given over period of about 90 minutes, followed by smaller weekly maintenance doses (2 mg/kg) that are administered over a shorter period of time, about 30 minutes. When administered in conjunction with other adjuvant cancer therapies (e.g., chemotherapy, hormone therapy), the anti-HER-2 monoclonal antibody is administered on the same or similar cycles as the other cancer therapy.

An anti-tumor effective amount of TTK antagonist that directly inhibits the expression or activity of a TTK protein in a tumor cell (e.g., inhibitory small molecules, neutralizing antibodies, inhibitory nucleic acids (e.g., siRNA, antisense nucleotides)) can be administered, for example, in a first cycle in which about the maximum tolerated dose of the antagonist is administered in one interval/dose, or in several closely spaced intervals (minutes, hours, days) with another/second cycle administered after a suitable off-therapy period (e.g., one or more weeks). Suitable dosing schedules and amounts for a TTK antagonist can be readily determined by a clinician of ordinary skill. Decreased toxicity of a particular TTK antagonist as compared to chemotherapeutic agents can allow for the time between administration cycles to be shorter. When used as an adjuvant therapy (to, e.g., surgery, radiation therapy, other primary therapies), an anti-tumor effective amount of a TTK antagonist is preferably administered on a dosing schedule that is similar to that of the other cancer therapy (e.g., chemotherapeutics), or on a dosing schedule determined by the skilled clinician to be more/most effective at inhibiting (reducing, preventing) tumor growth. A treatment regimen for an anti-tumor effective amount of a UK antagonist, for example, a small molecule, can be 0.001 mg/kg to about 100 mg/kg, from about 0.01 mg/kg to about 100 mg/kg, from about 0.01 mg/kg to about 10 mg/kg, from about 0.01 mg/kg to about 1 mg/kg, every 1 to 7 days over a period of about 4 to about 6 months. In addition, treatment regimen for an anti-tumor effective amount of a TTK antagonist, for example, an antibody, can be from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg every 1 to 7 days over a period of about 4 to about 6 months.

Accordingly, one aspect of the invention also relates to a method for directly inhibiting the growth of a tumor that expresses a TTK protein comprising administering to a patient with the tumor a therapeutically effective amount (e.g., an anti-tumor effective amount) of a TTK antagonist. In one embodiment, the TTK antagonist directly inhibits the growth of the tumor by inducing the apoptosis of the tumor cells or by inhibiting the proliferation of the tumor cells. The TTK antagonist can inhibit the expression (e.g., siRNA, antisense oligonucleotides) or activity (e.g., antibody, small molecule (e.g., SP600125, cincreasin), peptide, peptide mimetic) of a TTK protein, thereby directly inhibiting the growth of the cells of the tumor.

In another aspect, a TTK antagonist can be administered in a metronomic dosing regime, whereby a lower dose is administered more frequently relative to maximum tolerated dosing. A number of preclinical studies have demonstrated superior anti-tumor efficacy, potent antiangiogenic effects, and reduced toxicity and side effects (e.g., myelosuppression) of metronomic regimes compared to maximum tolerated dose (MTD) counterparts (Bocci, et al., *Cancer Res*, 62:6938-6943, (2002); Bocci, et al., *Proc. Natl. Acad. Sci.*, 100(22): 12917-12922, (2003); and Bertolini, et al., *Cancer Res*, 63(15):4342-4346, (2003)). Metronomic chemotherapy appears to be effective in overcoming some of the shortcomings associated with chemotherapy.

A TTK antagonist can be administered in a metronomic dosing regime to inhibit (reduce, prevent) angiogenesis in a patient in need thereof as part of an anti-angiogenic therapy. Such anti-angiogenic therapy may indirectly affect (inhibit, reduce) tumor growth by blocking the formation of new blood vessels that supply tumors with nutrients needed to sustain tumor growth and enable tumors to metastasize. Starving the tumor of nutrients and blood supply in this manner can eventually cause the cells of the tumor to die by necrosis and/or apoptosis. Previous work has indicated that the clinical outcomes (inhibition of endothelial cell-mediated tumor angiogenesis and tumor growth) of cancer therapies that involve the blocking of angiogenic factors (e.g., VEGF, bFGF, TGF-α, IL-8, PDGF) or their signaling have been more efficacious when lower dosage levels are administered more frequently, providing a continuous blood level of the antiangiogenic agent. (See Browder et al. *Can. Res.* 60:1878-1886, 2000; Folkman J., *Sem. Can. Biol.* 13:159-167, 2003). An anti-angiogenic treatment regimen has been used with a targeted inhibitor of angiogenesis (thrombospondin1 and platelet growth factor-4 (TNP-470)) and the chemotherapeutic agent cyclophophamide. Every 6 days, TNP-470 was administered at a dose lower than the maximum tolerated dose and cyclophophamide was administered at a dose of 170 mg/kg. Id. This treatment regimen resulted in complete regression of the tumors. Id. In fact, anti-angiogenic treatments are most effective when administered in concert with other anti-cancer therapeutic agents, for example, those agents that directly inhibit tumor growth (e.g., chemotherapeutic agents). Id.

Other Therapies

A therapeutically effective amount of a TTK antagonist can be administered alone, as an adjuvant therapy to a primary cancer therapy (surgery, radiation), with anti-angiogenic therapies (e.g., avastatin, endostatin, tumstatin, angiostatin) or as a primary therapy with other adjuvant therapies (e.g., chemotherapeutic, hormone).

The effectiveness of a therapy (e.g., the reduction or elimination of a tumor, the prevention or inhibition of tumor growth, the treatment or prevention of an angio genesis disorder, and/or the prevention or treatment of cancer metastasis) can be determined by any suitable method (e.g., in situ immunohistochemistry, imaging (MRI, NMR), 3H-thymidine incorporation).

The methods described herein comprise administering a TTK antagonist. The TTK antagonist may be administered to the individual in need thereof as a primary therapy (e.g., as the principal therapeutic agent in a therapy or treatment regimen); as an adjunct therapy (e.g., as a therapeutic agent used together with another therapeutic agent in a therapy or treatment regime, wherein the combination of therapeutic agents provides the desired treatment; "adjunct therapy" is also referred to as "adjunctive therapy"); in combination with an adjunct therapy; as an adjuvant therapy (e.g., as a therapeutic agent that is given to the subject in need thereof after the principal therapeutic agent in a therapy or treatment regimen has been given); or in combination with an adjuvant therapy (e.g., chemotherapy (e.g., dacarbazine (DTIC), Cis-platinum, cimetidine, tamoxifen, cyclophophamide), radiation therapy, hormone therapy (e.g., anti-estrogen therapy, androgen deprivation therapy (ADT), luteinizing hormone-releasing hormone (LH-RH) agonists, aromatase inhibitors (AIs, such as anastrozole, exemestane, letrozole), estrogen receptor modulators (e.g., tamoxifen, raloxifene, toremifene)), or biological therapy). Numerous other therapies can also be administered during a cancer treatment regime to mitigate the effects of the disease and/or side effects of the cancer treatment including therapies to manage pain (narcotics, acupuncture), gastric discomfort (antacids), dizziness (anti-veritgo medications), nausea (anti-nausea medications), infection (e.g., medications to increase red/white blood cell counts) and the like, all of which are readily appreciated by the person skilled in the art.

Thus, a TTK antagonist can be administered as an adjuvant therapy (e.g., with another primary cancer therapy or treatment). As an adjuvant therapy, the TTK antagonist can be administered before, after or concurrently with a primary therapy like radiation and/or the surgical removal of a tumor (s). In some embodiments, the method comprises administering a therapeutically effective amount of a TTK antagonist and one or more other therapies (e.g., adjuvant therapies, other targeted therapies). An adjuvant therapy (e.g., a chemotherapeutic agent) and/or the one or more other targeted therapies (e.g., a PLK1 antagonist) and the TTK antagonist can be co-administered simultaneously (e.g., concurrently) as either separate formulations or as a joint formulation. Alternatively, the therapies can be administered sequentially, as separate compositions, within an appropriate time frame (e.g., a cancer treatment session/interval such as 1.5 to 5 hours) as determined by the skilled clinician (e.g., a time sufficient to allow an overlap of the pharmaceutical effects of the therapies). The adjuvant therapy and/or one or more other targeted therapies (e.g., a PLK1 antagonist) and the TTK antagonist can be administered in a single dose or multiple doses in an order and on a schedule suitable to achieve a desired therapeutic effect (e.g., inhibition of tumor growth, inhibition of angiogenesis, and/or inhibition of cancer metastasis).

One or more agents that are a TTK antagonist can be administered in single or multiple doses. Suitable dosing and regimens of administration can be determined by a clinician and are dependent on the agent(s) chosen, pharmaceutical formulation and route of administration, various patient factors and other considerations. With respect to the administration of a TTK antagonist with one or more other therapies or treatments (adjuvant, targeted, cancer treatment-associated, and the like) the TTK antagonist is typically administered as a single dose (by e.g., injection, infusion, orally), followed by repeated doses at particular intervals (e.g., one or more hours) if desired or indicated.

The amount of the TTK antagonist to be administered (e.g., a therapeutically effective amount, an anti-tumor effective amount, an anti-angiogenesis effective amount, an anti-metastasis effective amount) can be determined by a clinician using the guidance provided herein and other methods known in the art and is dependent on several factors including, for example, the particular agent chosen, the subject's age, sensitivity, tolerance to drugs and overall well-being. For example, suitable dosages for a small molecule can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages for antibodies can be from about 0.01 mg/kg to about 300 mg/kg body weight per treatment and preferably from about 0.01 mg/kg to about 100 mg/kg, from about 0.01 mg/kg to about 10 mg/kg, from about 1 mg/kg to about 10 mg/kg body weight per treatment. Where the TTK antagonist is a polypeptide (linear, cyclic, mimetic), the preferred dosage will result in a plasma concentration of the peptide from about 0.1 µg/mL to about 200 µg/mL. Determining the dosage for a particular agent, patient and cancer is well within the abilities of one of skill in the art. Preferably, the dosage does not cause or produces minimal adverse side effects (e.g., immunogenic response, nausea, dizziness, gastric upset, hyperviscosity syndromes, congestive heart failure, stroke, pulmonary edema).

HER-2 Positive Tumor Therapy

Breast cancers that are positive for HER-2 expression represent a breast cancer subtype that is characterized by rapid, aggressive tumor growth and progression, a high-grade appearance under the microscope and is associated with a poor clinical outcome and poor prognosis. Despite the negative attributes associated with HER-2 positive cancers, a number of therapeutic agents have been developed which have some efficacy in the treatment of such cancers. For example, in HER-2 positive breast cancers, a therapeutic agent that inhibited HER-2 activity (e.g., an anti-HER-2 antibody), when used in conjunction with adjuvant therapies (e.g., chemotherapy, hormone therapy) reduced the risk of cancer recurrence or death by about half (Romond E. H. et al. *N Engl. J Med.* 353(16):1673-1684, 2005). Therapeutic agents that target HER-2 expression or activity include, for example, monoclonal antibodies (e.g., trastuzumab (Herceptin®, Genetech, Inc.)), small molecule compounds and antisense HER-2 oligonucleotides. An indication for a treatment involving administration of an anti-HER-2 agent can be confirmed using any suitable methods such as fluorescence in situ hybridization (FISH) which can be used to detect the presence of excess copies of the HER-2 gene in the tumor cells, or immunohistochemistry. However, as shown herein, there is a strong association between TTK expression in breast tumors and HER-2 positive breast cancer (see, e.g., Example 3).

Accordingly, in one embodiment of the method for treating cancer in a mammalian subject by administering to the subject a therapeutically effective amount of a TTK antagonist further comprises administering a HER-2 antagonist, such as trastuzumab.

Another aspect of the invention provides for a method of treating a TTK positive, HER-2 positive tumor comprising administering to a mammalian subject a therapeutically effective amount of a TTK antagonist and a therapeutically effective amount of a HER-2 antagonist, such as trastuzumab. As defined herein, HER-2 positive tumors are tumors overexpressing the HER-2 protein, generally due to the presence of extra copies of the HER-2 gene in the tumor cells. Overexpression of the HER-2 protein, which can be determined immunohistochemically in cultured, biopsied or surgical tumor tissue samples (or using other suitable methods). In a particular embodiment, the tumor is a HER-2 positive breast cancer tumor that also expresses TTK. Several types of breast cancer tumors (e.g., carcinoma) can be treated with a combination of anti-HER-2 and anti-TTK antagonists, including tumors associated with ductal breast cancer, lobular breast cancer and nipple breast cancer.

Another aspect of the invention provides for a method of treating a TTK positive, HER-2 positive, estrogen receptor negative tumor comprising administering to a mammalian subject a therapeutically effective amount of a TTK antagonist and a therapeutically effective amount of a HER-2 antagonist, such as trastuzumab. In a particular embodiment, the tumor is a HER-2 positive breast cancer tumor that also expresses a TTK. Several types of breast cancer tumors (e.g., carcinoma) can be treated with a combination of anti-HER-2 and anti-TTK antagonists, including ductal breast cancer, lobular breast cancer and nipple breast cancer.

In yet another aspect, the invention provides for a composition comprising a TTK antagonist and a HER-2 antagonist. In one embodiment, the composition comprises a TTK antagonist, a HER-2 antagonist and a physiologically or pharmaceutically acceptable carrier. In another embodiment, the composition comprises trastuzumab, a TTK antagonist and a physiologically or pharmaceutically acceptable carrier. In another embodiment, the composition comprises a small molecule which selectively binds a TTK protein, a HER-2 antagonist and a physiologically or pharmaceutically acceptable carrier. In yet another embodiment, the composition comprises trastuzumab, a small molecule which selectively binds a TTK protein and a physiologically or pharmaceutically acceptable carrier. Pharmaceutical compositions and formulations are discussed herein.

Basal-like Breast Cancer Tumor Therapy

Basal-like breast cancer represents another breast cancer subtype that is characterized by rapid, aggressive tumor growth and progression, a high-grade appearance under the microscope and is associated with a poor clinical outcome and poor prognosis. In general, basal-like breast cancers are estrogen receptor negative and express normal amounts of HER-2 protein, making these cancers particularly difficult to treat and diagnose. Thus, basal subtype breast cancers cannot be treated with ER-targeted or HER2 targeted therapies. As a result, basal subtype breast cancer is primarily treated with chemotherapy. Carey, L. A., *Breast Cancer Research*, 9(Suppl 1):S13 (2007). Basal-like breast cancer is common in women who have a BRCA gene mutation, in particular a BRCA1 gene mutation. Basal-like breast cancers typically express genes that are characteristic of basal breast cells, including basal cytokeratins (e.g., cytokeratin 5/6, cytokeratin 17), laminin, B4, HER1 and c-KIT, among others (Nielsen et al., *Clinical Cancer Research* 10:5367-5374 (2004)). Expression of genes that are characteristic of basal breast cells can be determined immunohistochemically in cultured, biopsied or surgical tumor tissue samples (or using other suitable methods). As shown herein, there is a strong association between TTK expression and basal-like breast cancer tumor samples and cell lines (see, e.g., Example 3).

Accordingly, in one aspect, the invention provides for a method of treating a TTK positive basal-like breast cancer tumor comprising administering to a mammalian subject a therapeutically effective amount of a TTK antagonist. The method can further comprise administering one or more other therapeutic agents used for the treatment of basal-like breast cancer.

Methods for Administration

According to the methods of the invention, a therapeutically effective amount (anti-tumor effective amount, anti-angiogenesis effective amount) is administered to a mammalian subject to treat cancer. The term "mammalian subject" is defined herein to include mammals such as primates (e.g., humans) cows, sheep, goats, horses, dogs cats, rabbits, guinea pigs, rats, mice or other bovine, ovine, equine, canine feline, rodent or murine species.

TTK antagonists can be administered in single or multiple doses. Suitable dosing and regimens of administration can be determined by a practitioner and are dependent on the agent(s) chosen, pharmaceutical formulation and route of administration, various patient factors and other considerations. With respect to the administration of a TTK antagonist with one or more other therapeutic agents (adjuvant, targeted, cancer treatment-associated), the antagonist is typically administered as a single dose (by e.g., injection, infusion), followed by repeated doses at particular intervals (e.g., one or more hours) if indicated or desired.

The amount of the TTK antagonist to be administered (e.g., therapeutically effective amount, anti-tumor effective amount, anti-angiogenesis effective amount) can be determined by a clinician using the guidance provided herein and other methods known in the art and is dependent on several factors including, for example, the particular agent chosen, the subject's age, sensitivity, tolerance to drugs and overall well-being. For example, suitable dosages for a small molecule can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Suitable dosages for antibodies can be from about 0.1 mg/kg to about 300 mg/kg body weight per treatment and preferably from about 0.01 mg/kg to about 100 mg/kg body weight per treatment. Preferably, the dosage does not cause, or produces minimal, adverse side effects (e.g., immunogenic response, nausea, dizziness, gastric upset, hyperviscosity syndromes, congestive heart failure, stroke, pulmonary edema). Where the TTK antagonist is a polypeptide (linear, cyclic, mimetic), the preferred dosage will result in a plasma concentration of the peptide from about 0.1 µg/mL to about 200 µg/mL. Determining the dosage for a particular agent, patient and cancer is well within the abilities of one of skill in the art.

A variety of routes of administration can be used including, for example, oral, dietary, topical, transdermal, rectal, parenteral (e.g., intravenous, intraaterial, intramuscular, subcutaneous injection, intradermal injection), intravenous infusion and inhalation (e.g., intrabronchial, intranasal or oral inhalation, intranasal drops) routes of administration, depending on the agent and the particular cancer to be treated. Administration can be local or systemic as indicated. The preferred mode of administration can vary depending on the particular agent chosen; however, oral or parenteral administration is generally preferred (e.g., to administer small molecule TTK antagonists).

The TTK antagonist can be administered to a mammalian subject as part of a pharmaceutical or physiological composition, for example, as part of a pharmaceutical composition comprising an antagonist of TTK and a pharmaceutically acceptable carrier. Formulations or compositions comprising a TTK antagonist or compositions comprising a TTK antagonist and one or more other targeted therapies (e.g., a HER-2 antagonist) will vary according to the route of administration selected (e.g., solution, emulsion or capsule). Suitable pharmaceutical carriers can contain inert ingredients which do not interact with the TTK antagonist. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

For example, nucleic acid-based TTK antagonists (e.g., siRNAs, antisense oligonucleotides, natural or synthetic nucleic acids, nucleic acid analogs) can be introduced into a mammalian subject of interest in a number of ways. For instance, nucleic acids may be expressed endogenously from expression vectors or PCR products in host cells or packaged into synthetic or engineered compositions (e.g., liposomes, polymers, nanoparticles) that can then be introduced directly into the bloodstream of a mammalian subject (by, e.g., injection, infusion). Anti-TTK nucleic acids or nucleic acid expression vectors (e.g., retroviral, adenoviral, adeno-associated and herpes simplex viral vectors, engineered vectors, non-viral-mediated vectors) can also be introduced into a mammalian subject directly using established gene therapy strategies and protocols (see e.g., Tochilin V. P. *Annu Rev Biomed Eng* 8:343-375, 2006; Recombinant DNA and Gene Transfer, Office of Biotechnology Activities, National Institutes of Health Guidelines).

Similarly, where the agent is a protein or polypeptide, the agent can be administered via in vivo expression of recombinant protein. In vivo expression can be accomplished by somatic cell expression according to suitable methods (see, e.g., U.S. Pat. No. 5,399,346). Further, a nucleic acid encoding the polypeptide can also be incorporated into retroviral, adenoviral or other suitable vectors (preferably, a replication deficient infectious vector) for delivery, or can be introduced into a transfected or transformed host cell capable of expressing the polypeptide for delivery. In the latter embodiment, the cells can be implanted (alone or in a barrier device), injected or otherwise introduced in an amount effective to express the polypeptide in a therapeutically effective amount.

Diagnostic and Prognostic Methods

The present invention encompasses diagnostic and prognostic methods that comprise assessing expression of TTK in a suitable tumor sample from a subject. For diagnostic methods of the invention, expression of TTK by the tumor, or increased expression of TTK by the tumor relative to a suitable control, indicates that the subject has a non-luminal breast cancer and/or that the subject is a candidate for an anti-cancer therapy using a antagonist and/or the subject is a candidate for an aggressive cancer therapy.

For prognostic methods of the invention, expression of TTK by the tumor, or increased expression of TTK by the tumor relative to a suitable control, indicates a poor prognosis. The prognosis can be a prognosis for patient survival, a prognosis for risk of metastases and/or a prognosis for risk of relapse. As described herein, a strong association exists between high TTK expression in breast cancer samples and reduced patient survival, increased risk of metastases and increased risk of relapse (see, e.g., Example 2).

Suitable tumor samples for these methods include a tissue sample, a biological fluid sample, a cell(s) (e.g., a tumor cell) sample, and the like. Any means of sampling from a subject, for example, by blood draw, spinal tap, tissue smear or scrape, or tissue biopsy can be used to obtain a sample. Thus, the sample can be a biopsy specimen (e.g., tumor, polyp, mass (solid, cell)), aspirate, smear or blood sample. The sample can be from a tissue that has a tumor (e.g., cancerous growth) and/or tumor cells, or is suspecting of having a tumor and/or tumor cells. For example, a tumor biopsy can be obtained in an open biopsy, a procedure in which an entire (excisional biopsy) or partial (incisional biopsy) mass is removed from a target area. Alternatively, a tumor sample can be obtained through a percutaneous biopsy, a procedure performed with a needle-like instrument through a small incision or puncture (with or without the aid of a imaging device) to obtain individual cells or clusters of cells (e.g., a fine needle aspiration (FNA)) or a core or fragment of tissues (core biopsy). The biopsy samples can be examined cytologically (e.g., smear), histologically (e.g., frozen or paraffin section) or using any other suitable method (e.g., molecular diagnostic methods). A tumor sample can also be obtained by in vitro harvest of cultured human cells derived from an individual's tissue. Tumor samples can, if desired, be stored before analysis by suitable storage means that preserve a sample's protein and/or nucleic acid in an analyzable condition, such as quick freezing, or a controlled freezing regime. If desired, freezing can be performed in the presence of a cryoprotectant, for example, dimethyl sulfoxide (DMSO), glycerol, or propanediol-sucrose. Tumor samples can be pooled, as appropriate, before or after storage for purposes of analysis. The tumor sample can be from a patient who has a TTK positive cancer, for example, a TTK positive non-luminal breast cancer (e.g., a basal-like cancer, a HER-2 positive cancer).

Suitable assays can be used to assess the presence or amount of a TTK in a sample (e.g., biological sample). Methods to detect a TTK protein or peptide can include immunological and immunochemical methods like flow cytometry (e.g., FACS analysis), enzyme-linked immunosorbent assays (ELISA), including chemiluminescence assays, radioimmunoassay, immunoblot (e.g., Western blot), and immunohistology, or other suitable methods such as mass spectroscopy. For example, antibodies to TTK can be used to determine the presence and/or expression level of TTK in a sample directly or indirectly using, for instance, immunohistology. For instance, paraffin sections can be taken from a biopsy, fixed to a slide and combined with one or more antibodies by suitable methods.

Methods to detect a TTK gene or expression thereof (e.g., DNA, mRNA) include TTK nucleic acid amplification and/or visualization. To detect a TTK gene or expression thereof, nucleic acid can be isolated from an individual by suitable methods which are routine in the art (see, e.g., Sambrook et al., 1989). Isolated nucleic acid can then be amplified (by e.g., polymerase chain reaction (PCR) (e.g., direct PCR, quantitative real time PCR, reverse transcriptase PCR), ligase chain reaction, self sustained sequence replication, transcriptional amplification system, Q-Beta Replicase, or the like) and visualized (by e.g., labeling of the nucleic acid during amplification, exposure to intercalating compounds/dyes, probes). TTK gene or expression thereof can also be detected using a nucleic acid probe, for example, a labeled nucleic acid probe (e.g., fluorescence in situ hybridization (FISH)) directly in a paraffin section of a tissue sample taken from, e.g., a tumor biopsy, or using other suitable methods. TTK gene or expression thereof can also be assessed by Southern blot or in solution (e.g., dyes, probes). Further, a gene chip, microarray, probe (e.g., quantum dots) or other such device (e.g., sensor, nanonsensor/detector) can be used to detect expression and/or differential expression of a TTK gene.

In one embodiment, a TTK positive non-luminal breast cancer can be diagnosed by detecting expression of a TTK gene product (e.g., TTK mRNA, TTK protein) in a sample from a patient. Thus, the method does not require that TTK expression in the sample from the patient be compared to the expression of TTK in a control. The presence or absence of TTK can be ascertained by the methods described herein or other suitable assays. In another embodiment, an increase in expression of TTK can be determined by comparison of TTK expression in the sample to that of a suitable control. Suitable controls include, for instance, a non-neoplastic tissue sample from the individual, non-cancerous cells, non-metastatic cancer cells, non-malignant (benign) cells or the like, or a suitable known or determined standard. The control can be a known or determined typical, normal or normalized range or level of expression of a TTK protein or gene (e.g., an expression standard). Thus, the method does not require that expression of the gene/protein be assessed in a suitable control. TTK expression can be compared to a known or determined standard.

The present invention will now be illustrated by the following Examples, which are not intended to be limiting in any way.

EXEMPLIFICATION

Material and Methods siRNAs and reagents: The following siRNAs targeting the human TTK protein kinase gene (SEQ ID NO:1) (Genbank Accession No. M86699, see also FIGS. 13A-13B) were used:

```
siRNA1:  5'-GCAAUACCUUGGAUGAUUA-3'; (SEQ ID NO: 3)
siRNA2:  5'-GGUAUUAACUGCCCAAGAA-3'; (SEQ ID NO: 4)
siRNA3:  5'-GCACGUGACUACUUUCAAA-3'; (SEQ ID NO: 5)
siRNA4:  5'-GAUAAGAUCAUCCGACUUU-3'. (SEQ ID NO: 6)
```

Non-targeting control siRNA (siCONTROL), which targets a firefly luciferase gene sequence, was purchased from Dharmacon. Transfection reagent Lipofectamine 2000 was purchased from Invitrogen Canada, Burlington, ON, Canada. The reagents for the Sulforhodamine B (SRB) cell viability assay were from Sigma Canada, Oakville, ON, Canada. TTK antibody (C-19) was purchased from Santa Cruz Biotechnology, Inc., and β-actin antibody (A2066) was purchased from Sigma-Aldrich Co.

TTK QPCR: Total RNA (tRNA) was prepared using Trizol Reagent (Invitrogen Corporation) according to manufacturer's instructions. tRNA was DNase treated at room temperature for 15 min. Primers were designed to amplify short segments of target cDNA (amplicon) with a size range of 100-150 bp. Quantitative real time PCR (QRT-PCR) reactions were performed using One Step SYBR QPCR Kit (Invitrogen Corporation, Cat #117146-100) according to manufacturer's instructions. Direct detection of the PCR product was monitored by measuring the increase in fluorescence caused by the binding of SYBR Green I dye to the double-stranded (ds) DNA product using the RealPlex4 System (Eppendorf). The conditions for the assay were 53° C. for 20 min, 95° C. for 5 min, followed by 42 cycles of 95° C. for 15 sec, 60° C. for 30 sec and 72° C. for 30 sec. All PCR efficiencies were above 95%. Relative quantification of gene expression was performed using the standard curve method comprising six serial dilution points (ranging from 0.32 ng to 1000 ng). Each tRNA sample was analyzed by calculating the average $C_t$ values from triplicate PCR reactions. β-Actin gene expression was used for data normalization. Data were expressed as a mean±SD. Amplification primers for TTK are 5'-TGATG-GCAAACAACCCAGAGG-3' (forward) (SEQ ID NO:7) and 5'-TTGCTTGACTGTAACGACCAAT-3' (reverse) (SEQ ID NO:8), and β-Actin are 5'-GGCACTCTTCCAGCCTTC-CTT-3' (forward) (SEQ ID NO:9) and 5'-TCTCCTTCTG-CATCCTGTCG-3' (reverse) (SEQ ID NO:10).

TTK Western: Whole cell lysates (40 tag) were resolved by SDS-PAGE and transferred to nitrocellulose membranes (Invitrogen Corporation) for immunoblot analysis using TTK (1/500) and β-actin (1 µg/ml) rabbit polyclonal antibodies. For the detection, peroxidase-Goat Anti-Rabbit IgG (1/5000; Amersham Biosciences) conjugated antisera was used. The proteins were visualized using ECL (Pierce).

TTK Microarray expression profiling: All gene expression analyses were done in three individual datasets and in a combined dataset. The datasets were combined after normalizing expression values, e.g. logratios, of each gene by mean and standard deviation in each dataset. Regression models in the combined dataset contained a dataset term in addition to the logratio term. To verify that results did not depend on normality assumption, another combined dataset was assembled using logratio ranks, computed separately in each dataset and scaled to vary from 0 to 1. The same analyses were performed and general agreement with the results from the normalized log ratio dataset was verified.

Transfection of siRNAs into normal breast and breast cancer cell lines: Different normal breast and breast cancer cell lines were used for siRNA transfection. Cells were seeded at various concentrations, ranging from 1500 to 6000 per well according to cell growth rate, into 96 well plates. 40 nM individual siRNAs or 40 nM siRNA pool including four individual siRNAs at 10 nM each were transfected into cells using Lipofectamine-2000 24 hrs after cell seeding. Cells were then incubated at 37° C. for five days before cell viability assay were conducted.

Sulforhodamine B (SRB) assay: SRB assay was performed to assess cell survival. SRB is a water-soluble dye that binds to the basic amino acids of the cellular proteins. Thus, colorimetric measurement of the bound dye provides an estimate of the total protein mass and is related to the cell number. The cells were fixed in situ by gently aspirating off the culture media and adding 50 µl ice cold 10% Tri-chloroacetic Acid (TCA) per well and incubate at 4° C. for 30-60 min. The plates were washed with tap water five times and allowed to air dry for 5 min. 50 of 0.4% (w/v) Sulforhodamine B solution in 1% (v/v) acetic acid was added per well and incubated for 30 min at RT for staining. Following staining, plates were washed four times with 1% acetic acid to remove any unbound dye and then allowed to air dry for 5 min. The stain was solubilized with 100 µl of 10 mM Tris pH 10.5 per well. Absorbance was read at 570 nm. The cell survival percentage after each siRNA(s) knock down was calculated over the non-silencing control siCTRL or siPOOL as well as siTOX as a transfection efficiency control.

Colony formation in soft agar: Colony formation in soft agar: Cells were transfected with 40 nM individual siRNAs, 40 nM siRNA pool including four individual siRNAs at 10 nM each or 40 nM non-silencing control siCONTROL using Lipofectamine 2000 Transfection Reagent (Invitrogen Corporation), mixed with culture medium containing 0.7% agar in 6-well plates and cultured at 37° C. After 2 weeks, the top layer of the culture was stained with 0.2% p-iodonitrotetrazolium violet and colonies were counted using a Sorcerer Colony Counter (Optomax).

SP600125 experiment: Compound SP600125 was purchased from Biomol International (PA, USA). 10 mM stock was prepared in 100% DMSO. Cells were seeded at various numbers, ranging from 1500 to 4000 per 80 µl in each well according to cell growth rate, into 96 well plates, 24 hours before compound overlay. The 10 mM SP600125 compounds stock in 100% DMSO was diluted with Opti-MEM I Reduced-Serum Medium (Invitrogen, Burlington, ON, Canada) to concentrations range from 50 nM to 250 µM. 20 µl from each concentration was overlay to cells to make the final concentrations range from 10 nM to 50 µM. The cells were cultured for 5 days before Sulforhodamine B assay. SRB assay is performed to assess cell survival. SRB is a water-soluble dye that binds to the basic amino acids of the cellular proteins. Thus, colorimetric measurement of the bound dye provides an estimate of the total protein mass that is related to the cell number. the cells are fixed in situ by gently aspirating off the culture media and adding 50 ice cold 10% Tri-chloroacetic Acid (TCA) per well and incubate at 4° C. for 30-60 min, The plates are washed with tap water five times and allowed to air dry for 5 min. Add 50 µl 0.4% (w/v) Sulforhodamine B solution in 1% (v/v) acetic acid per well and incubate for 30 min at RT for staining. Following staining, plates are washed four times with 1% acetic acid to remove any unbound dye and then allowed to air dry for 5 min. Stain is solubilized with 100u1 of 10 mM Tris pH 10.5 per well. Absorbance is read at 570 nm. The cell survival percentage in each compound concentration was calculated over the cell DMSO control, which was growing in the presence of 0.1% DMSO (0.5% in the case of 50 µM compounds). The $GI_{50}$ were calculated using GraphPad PRISM software.

EXAMPLE 1

TTK Expression in Normal and Cancer Cells

Microarray expression analysis revealed that expression of TTK RNA in physiologically normal human tissues is restricted to fetal liver, placenta, testis, thymus and uterus (FIG. 1). Little detectable expression was observed in normal breast tissue. However, TTK RNA (FIG. 2A) and protein (FIG. 2B) was found to be expressed in several different breast cancer cell lines, with non-luminal breast cancer cell lines displaying the highest levels of TTK protein (FIG. 2B).

These results indicate that TTK is a target for breast cancer therapy.

EXAMPLE 2

High TTK Expression is Associated with Poor Prognosis in Breast Cancer Patients

Figure 6:
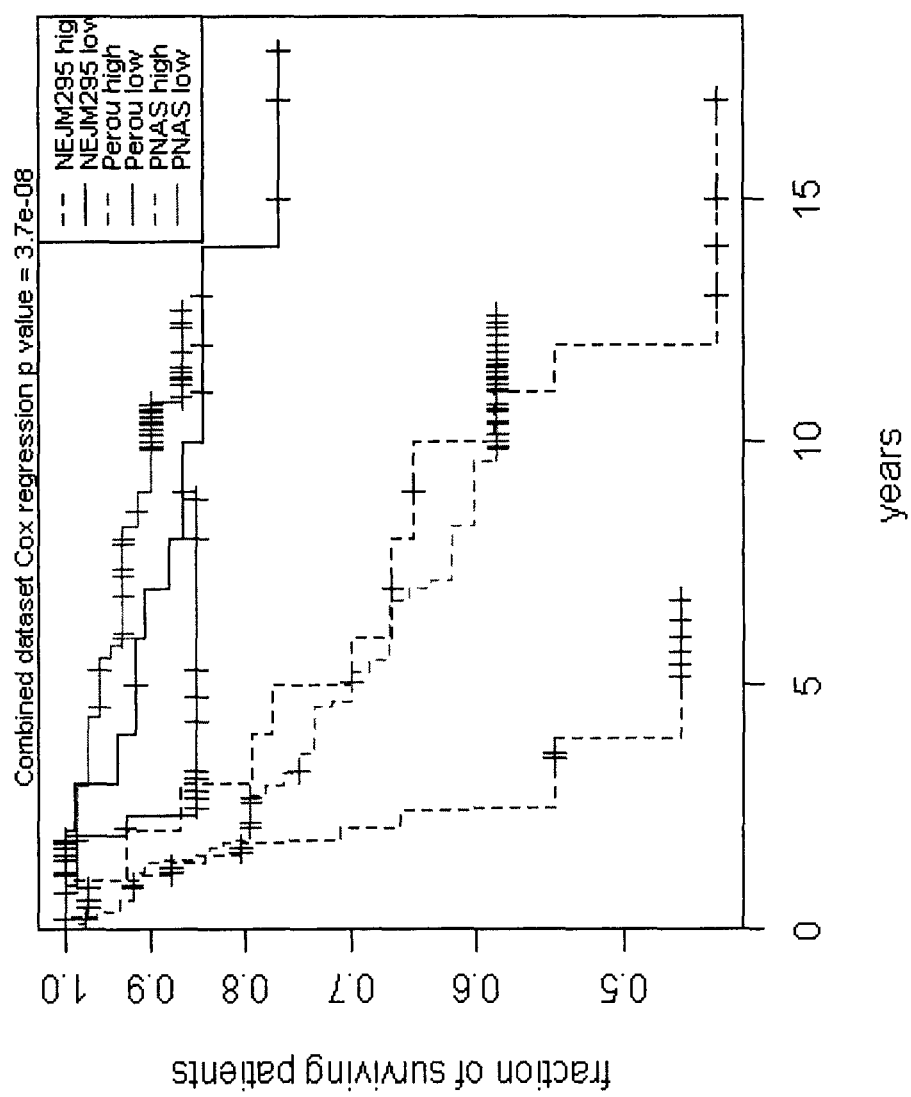
FIG. 6 is a graph illustrating a strong association (p=3.7E-08) between high TTK expression in breast and reduced patient survival in three data sets (NEJM, Perou, PNAS).

The association between TTK expression and survival in patients with breast cancer was evaluated using three data sets (NEJM 295 (Hu, et al., The molecular portraits of breast tumors are conserved across microarray platforms. *BMC Genomics* 7:96 (2006)), Perou (van di Vijver, M. J., et al., A gene-expression signature as a predictor of survival in breast cancer. *N Engl. J. Med.* 347(25):1999-2009 (2002)), and PNAS (Miller, L. D., et al. An expression signature for p53 status in human breast cancer predicts mutation status, transcriptional effects, and patient survival. *Proc. Natl. Acad. Sci. USA* 102(38):13550-5) (2005)). A strong association between high TTK expression and reduced survival was discovered in each of the three data sets (FIG. 6). The Cox regression p value for the combined data set was 3.7e-08.

Figure 7:
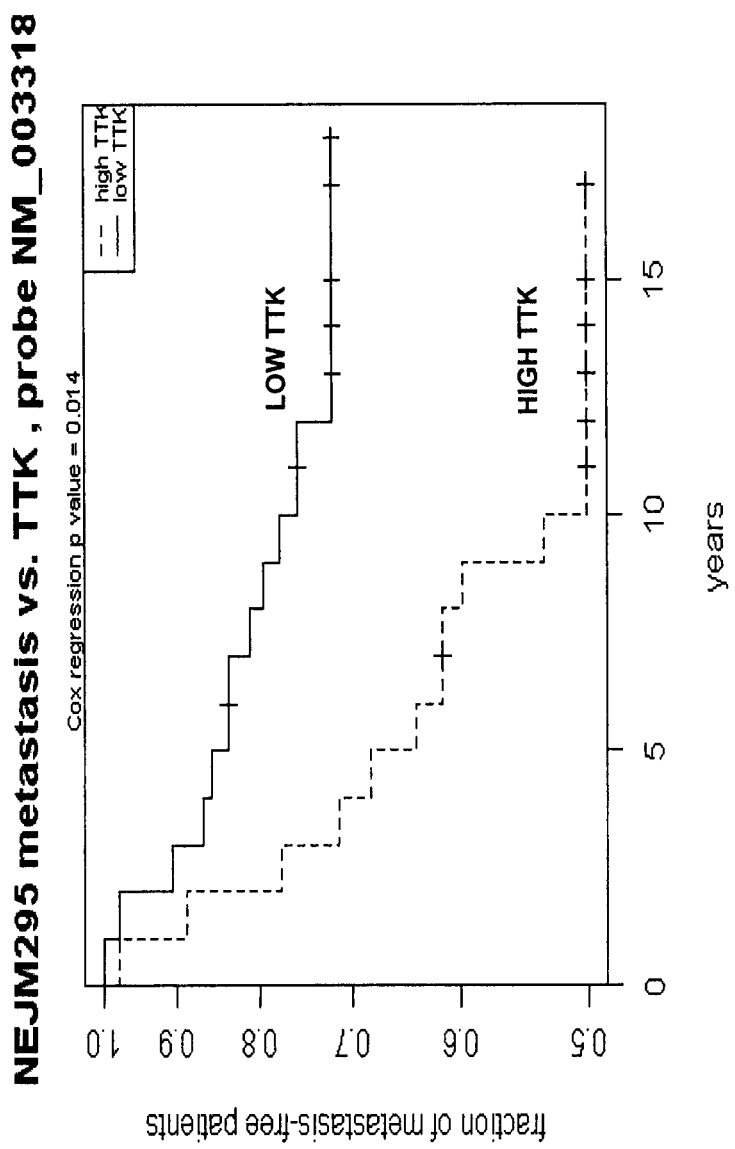
FIG. 7 is a graph illustrating an association (p=0.014) between high TTK expression in breast and increased risk of developing metastases.

In addition, the association between TTK expression and risk of developing metastases was also evaluated in patients with breast cancer. High TTK expression was associated with an increased risk of metastasis (FIG. 7). The Cox regression p value for the data set was 0.014.

Figure 8A:
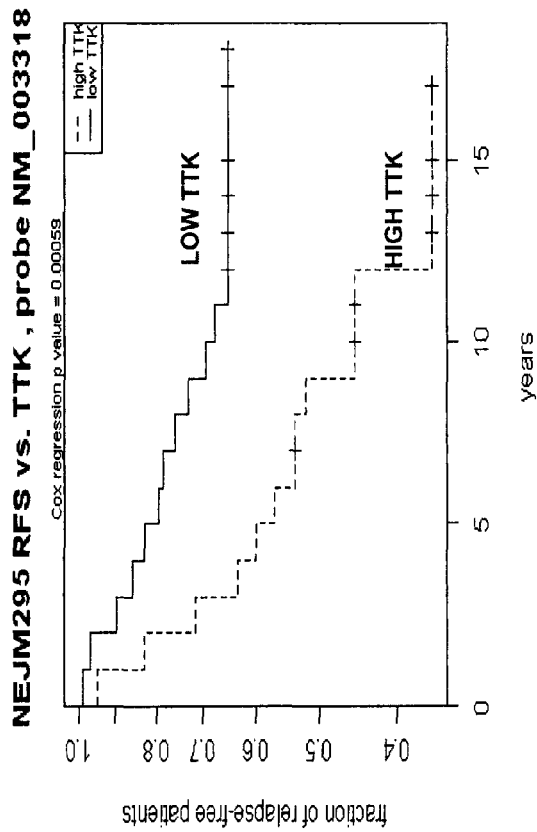
FIGS. 8A and 8B are graphs illustrating the association between TTK expression in breast and risk of relapse in two data sets (NEJM295, Perou).
Figure 8B:
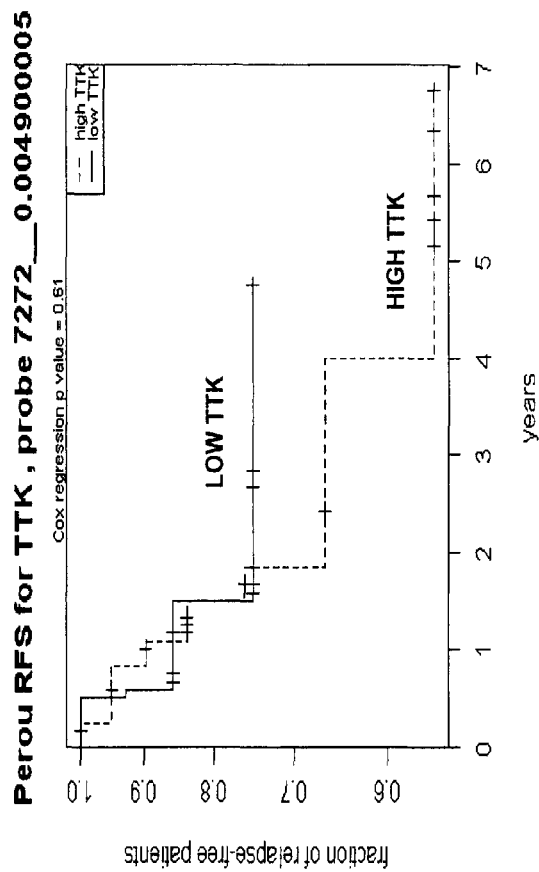

The association between TTK expression and risk of relapse was also evaluated using two data sets (NEJM295, Perou) (FIGS. 8A-8B). High TTK expression was associated with an increased risk of breast cancer relapse in the NEJM295 data set (FIG. 8A). The Cox regression p value for this data set was 0.00059.

Survival analysis was performed using Cox regression of survival times vs. gene expression log ratios, followed by the estimation of false discovery rates by Benjamini and Hochberg's method. NEJM 295 dataset provided data on recurrence and survival; Perou dataset on recurrence, metastasis, and survival; PNAS dataset on survival only; the combined dataset could be analyzed for survival, i.e., risk of death, only. High expression of TTK was associated with higher risks of recurrence, metastasis, and death in all datasets where such data were available, as well as in the combined dataset ($P<0.05$). These associations were observed in all cancers combined and in ER-positive cancers as a subgroup. A strong association of TTK expression with poor survival was also observed in p53$^-$ cancers in the PNAS dataset ($P<0.05$).

Tumor gene expression profiles were classified into subtypes defined by Hu et al. (2006). The classification of the NEJM 295 dataset was provided by its authors; Perou and PNAS datasets were classified into Luminal A, Luminal B, Basal-like and HER2+/ER− subtypes using the intrinsic gene set defined by Hu et al. Different subtypes were compared to each other and, where available, to normal controls.

NEJM 295 dataset was the only one that contained a normal control group. All cancers as a group and individual subtypes were compared to the control group using t tests. Significantly higher than normal expression of TTK, with p values <0.05 and false discovery rates <0.1, was detected in all cancers as a group and in Basal-like, Luminal B, and HER2+/ER− subtypes. The over-expression was the highest and most significant in the basal-like subtype, where it was, on average, 8-fold higher than normal.

An additional analysis was performed on the NEJM 295 dataset to determine if a fraction of cancers expressed a gene significantly outside of the normal range. This analysis was designed to detect over-expression in a subset of a potentially heterogeneous population of cancers. The normal range was defined as the mean+/−3 standard deviations of the normal control group. The fractions of tumor samples that fell above and below this range were recorded as percentages of the total number of tumors, in all cancers as a group and in individual subtypes. TTK was found to be over-expressed in 38% of all tumors and in 85% of basal-like tumors.

To verify over-expression of TTK in cancers compared to normal controls, we performed similar analyses in an additional dataset (Richardson et al., X chromosomal abnormalities in basal-like human breast cancer. Cancer Cell 9: 121-132 (2006)) that contained a normal control group. In the Richardson dataset, TTK appeared to be over-expressed, on average, 20-fold in all cancers and 37-fold in basal-like cancers; 100% of basal-like cancers expressed TTK above the normal range.

Different tumor subtypes were compared to each other using one way ANOVA and pair-wise t tests in all three datasets. There were statistically significant differences in TTK expression between different tumor subtypes in all 3 datasets, with estimated false discovery rates in $10^{-19}$-$10^{-31}$ range for the ANOVA p values. Expression was highest in basal-like tumors and lowest in normal controls in NEJM 295 dataset. Therefore, higher TTK expression was associated with more aggressive subtypes of breast cancer.

EXAMPLE 3

Validation of TTK as a Target for Breast Cancer Therapy

To validate TTK as a target for breast cancer therapy, the biological effects of TTK antagonists were investigated.

A. siRNA Antagonists

Figure 9A:
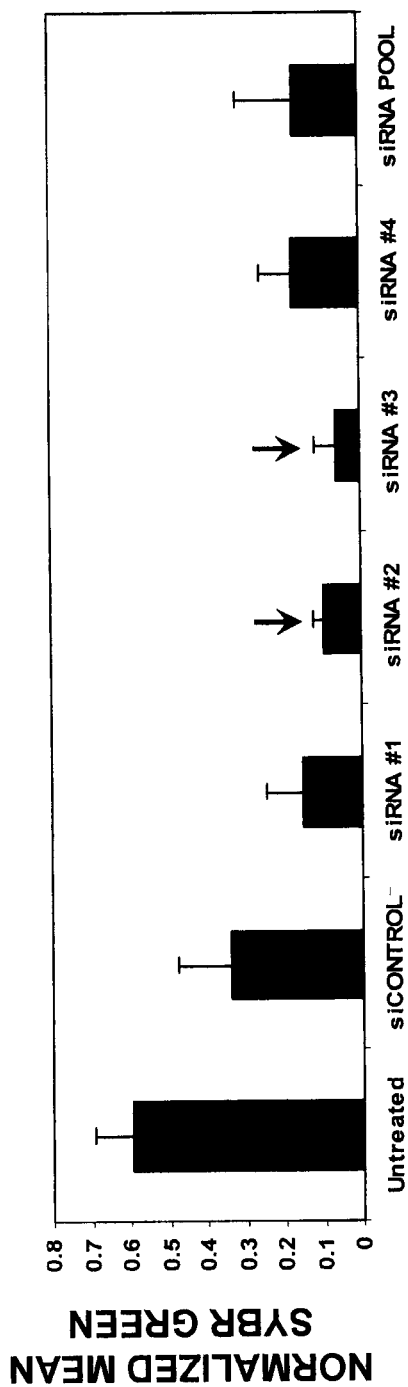
FIG. 9A is a graph illustrating siRNA-mediated knockdown of TTK RNA expression levels in MD-MB-468 breast cancer cells treated with one of four different siRNAs that target human TTK (siRNA #1, siRNA #2, siRNA #3, siRNA #4), as determined by quantitative polymerase chain reaction (QPCR). siCONTROL is a non-targeting siRNA that targets firefly luciferase. siRNA POOL is a combination of siRNA #1, siRNA #2, siRNA #3 and siRNA #4. siRNA #2 and siRNA #3 display a TTK knockdown efficiency of greater than 70% (see downward pointing arrows).

TTK expression was inhibited using RNA interference. MD-MB-468 breast cancer cells were transfected with a 40 nM concentration of one of four individual siRNAs that target different TTK mRNA sequences (siRNA #1, siRNA #2, siRNA #3, siRNA #4), a pool of the four TTK-targeting siRNAs (siRNA POOL), or a non-targeting control siRNA (siCONTROL) that targets firefly luciferase mRNA. Total RNA was isolated 48 hours post-transfection and TTK mRNA levels were determined by quantitative reverse-transcriptase polymerase chain reaction. TTK mRNA levels were normalized over beta-actin mRNA levels. Of the four TTK-targeting siRNAs, siRNAs #2 and #3 showed greater than 70% knockdown efficiency (FIG. 9A).

Figure 9B:
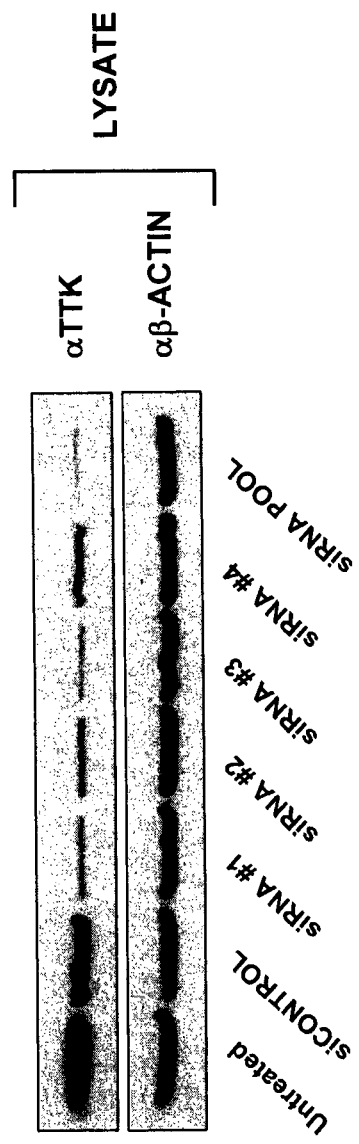
FIG. 9B is a picture of a Western blot depicting siRNA-mediated knockdown of TTK protein expression in lysates of MD-MB-468 breast cancer cells treated with one of four different siRNAs that target human TTK (siRNA #1, siRNA #2, siRNA #3, siRNA #4). siCONTROL is a non-targeting siRNA that targets firefly luciferase. siRNA POOL is a combination of siRNA #1, siRNA #2, siRNA #3 and siRNA #4. β-actin levels serve as a loading control.

In addition, Western blot analysis of TTK protein levels in lysates of MD-MB-468 breast cancer cells that had been transfected with siRNA revealed that transfection with any of the four TTK-targeting siRNAs, as well as the siRNA POOL, but not the siCONTROL siRNA, resulted in significantly reduced levels of TTK protein (FIG. 9B).

To assess the effects of TTK knockdown on the viability of breast cancer cells, various breast cancer cell lines were transfected with each of the four TTK-targeting siRNAs individually, the pooled siRNA containing all four of the TTK-targeting siRNAs, or the siCONTROL siRNA, all at a concentration of 40 nM. At day 5 post-transfection, the viability of the cells was determined using the SRB assay described herein. TTK expression levels post-transfection with the targeting siRNA were normalized over TTK levels following transfection with the non-silencing control. siRNA-mediated depletion of TTK levels substantially inhibited the viability of breast cancer cells in 7 out of 12 different breast cancer cell lines, including 3 basal-like breast cancer cell lines (Table 1).

TABLE 1

TTK knockdown inhibits viability of several different breast cancer cell lines (% survival).

|  | MDA-MB-468 | MCF-7 | MDA-MB-435 | SKBr-3 | CAMA-1 | Hs578T | MDA-MB-231 | T-47D | HCC1419 | MDA-MB-453 | BT474 | MDA-MB-330 |
|---|---|---|---|---|---|---|---|---|---|---|---|---|
| siRNA #1 | 0.69 | 0.27 | 0.78 | 0.32 | 0.46 | 1.02 | 0.21 | 0.62 | 0.91 | 0.33 | 0.64 | 0.31 |
| siRNA #2 | 0.00 | 0.27 | 0.25 | 0.34 | 0.30 | 1.25 | −0.09 | 0.44 | 0.75 | −0.04 | 0.66 | 0.38 |
| siRNA #3 | 0.27 | 0.23 | 0.60 | 0.49 | 0.52 | 0.53 | 0.23 | 0.74 | 0.91 | 0.18 | 0.83 | 0.63 |
| siRNA #4 | 1.46 | 0.63 | 0.93 | 0.91 | 0.77 | 1.16 | 0.58 | 1.19 | 1.05 | 0.56 | 0.90 | 0.72 |
| siRNA POOL | 0.34 | 0.28 | 0.57 | 0.48 | 0.34 | 0.65 | 0.24 | 0.78 | 0.97 | 0.66 | 0.98 | 0.55 |

TABLE 1-continued

TTK knockdown inhibits viability of several different breast cancer cell lines (% survival).

| MDA-MB-468 | MCF-7 | MDA-MB-435 | SKBr-3 | CAMA-1 | Hs578T | MDA-MB-231 | T-47D | HCC 1419 | MDA-MB-453 | BT 474 | MDA-MB-330 |
|---|---|---|---|---|---|---|---|---|---|---|---|

TTK expression levels were normalized over siCONTROL. Basal cell lines are MDA-MB-469, MDA-MB-435, Hs578T, and MDA-MB-231. Numbers in italics signify inhibition of greater than 50%.

Figure 10A:
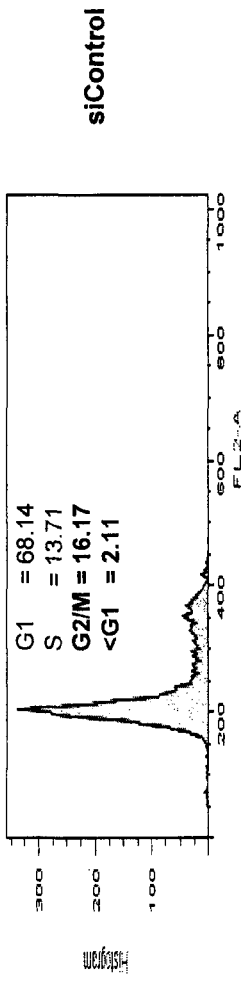
FIG. 10A-10C is a series of fluorescence histograms illustrating flow cytometry analysis of MCF7 breast cancer cells treated with one of two TTK-targeting siRNAs (TTK siRNA #2 (FIG. 10B), TTK siRNA #3 (FIG. 10C)) or non-targeting control siRNA that targets firefly luciferase (siCONTROL) (FIG. 10A). Treatment of the cells with TTK siRNA #2 or TTK siRNA #3, but not siCONTROL siRNA, caused apoptosis of the cancer cells, indicated by increased G2/M and <G1 populations.
Figure 10B:
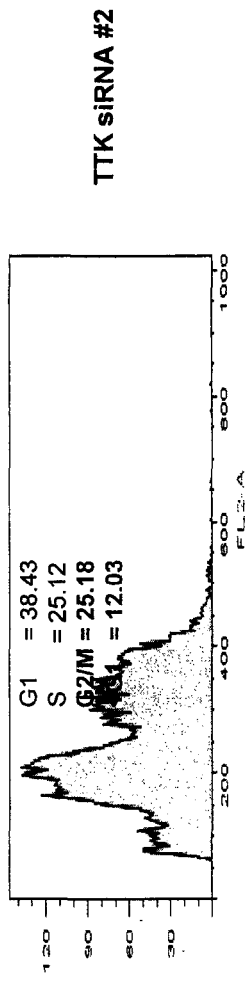
Figure 10C:
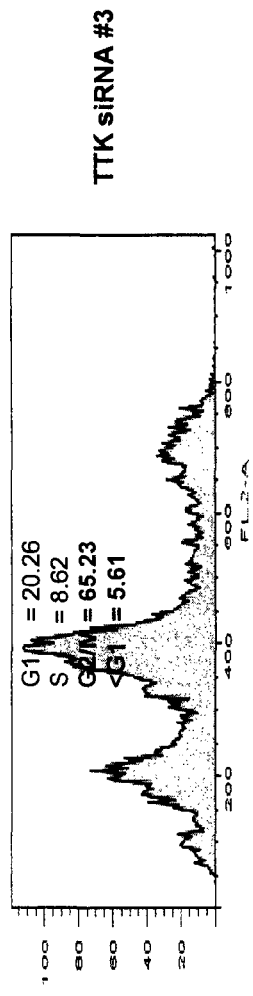
Figure 12:
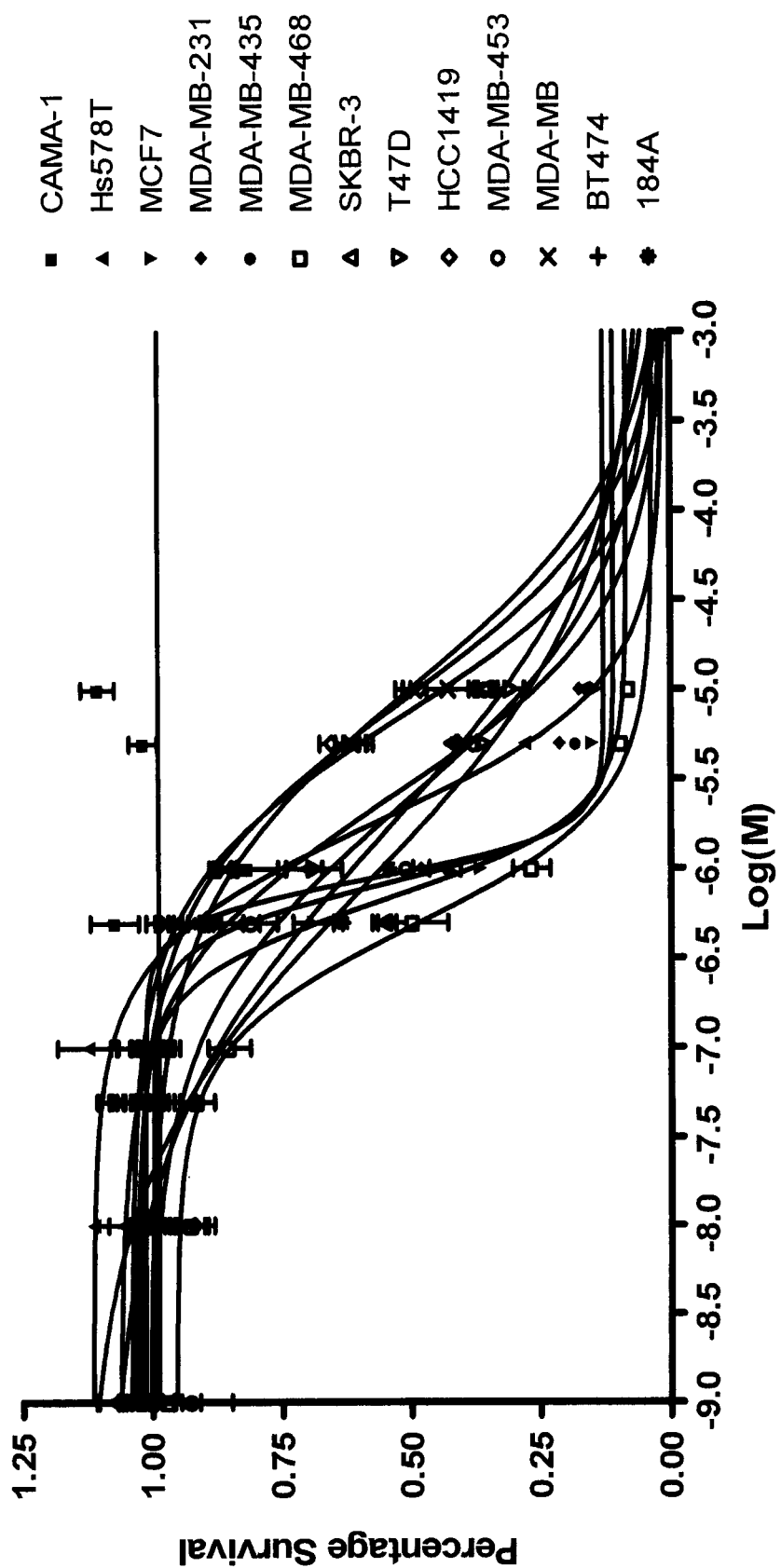
FIG. 12 is a graph illustrating reduced survival of breast cancer cells from several different breast cancer cell lines following treatment with SP600125, a small molecule antagonist of TTK.

To assess the effects of TTK knockdown on the physiology of normal breast and breast cancer cell lines, luminal (MCF7) or basal-like (MDA-MB-435, MDA-MB-468) breast cancer cell lines, a lung cancer cell line (A549) and a normal breast cell line (184A1) each were transfected with 40 nM of TTK-targeting siRNA #2, siRNA #3, the pooled siRNA containing all four of the TTK-targeting siRNAs, or the siCONTROL siRNA. At day 3 post-transfection, the cell cycle profile of the transfected cells was analyzed by flow cytometry to determine the effects of TTK knockdown on cell cycle arrest and cell death. The results are presented in Table 2 and FIG. 10. Depletion of TTK in cells transfected with TTK-targeting siRNAs caused significant cell cycle arrest and cell death.

To determine the effects of siRNA-mediated knockdown of TTK gene expression on anchorage-independent cell growth in breast cancer cells, T-47D breast cancer cell line was transfected with either the siRNA#2 or siRNA#3 TTK-targeting siRNA, the siRNA POOL containing 4 TTK-targeting siRNAs or the siCONTROL non-targeting siRNA. Following transfection colony formation in soft agar was assessed. Transfection of T-47D cells with siRNA#2, siRNA#3 or the siRNA POOL resulted in a reduction in both colony size and number, relative to the siCONTROL-transfected cells, in two independent experiments (FIGS. 11A-11B).

TABLE 2

TTK knockdown induces cell cycle arrest and cell death in some cancer cell lines, but not in normal cell lines.

| CELL LINE | siCONTROL (Neg. Control) | | TTK siRNA #2 | | TTK siRNA #3 | |
|---|---|---|---|---|---|---|
| | G2/M | <G1 | G2/M | <G1 | G2/M | <G1 |
| MCF-7 (Luminal) | 16.17 | 2.11 | 25.18 | 12.03 | 65.23 | 5.61 |
| MDA-MB-435 (Basal) | 18.77 | 0.85 | 19.89 | 4.69 | 40.08 | 2.66 |
| MDA-MB-468 (Basal) | 20.59 | 4.09 | 15.72 | 15.10 | 28.41 | 11.12 |
| 184A1 (Normal) | 10.35 | 1.03 | 27.75 | 5.35 | 17.49 | 3.92 |
| A549 (Lung) | 10.57 | 0.84 | 20.58 | 6.03 | 24.87 | 11.38 |

B. Small Molecule Antagonist

To assess the effects of inhibition of TTK activity on the viability of breast cancer cell lines, varying concentrations of SP600125, a small molecule TTK antagonist (Schmidt et al., *EMBO Reports* 6(9): 866-872 (2005)), in 0.1% DMSO, were added to the culture media of several different breast cancer cell lines 24 hr after the cells were seeded. Cell viability was assessed using the SRB assay described herein, which was performed 5 days after the addition of SP600125 to the culture media. Prism software was used to calculate $GI_{50}$ (concentration of the compound required to achieve 50% growth inhibition) (Table 3). Treatment of multiple cancer cell lines with compound SP600125 inhibited proliferation of cancer cells in a dose dependent manner with a $GI_{50}$ at low μM levels, suggesting TTK antagonists have anti-cancer activity.

TABLE 3

Concentrations of compound SP600125 required to achieve 50% growth inhibition ($GI_{50}$) for various cell lines.

| | Cell line | | | | | |
|---|---|---|---|---|---|---|
| | CAMA-1 | Hs578T | MCF-7 | MDA-MB-231 | MDA-MB-435 | MDA-MB-468 | SKBR-3 |
| $GI_{50}$ (μM) | N/A | 1.839 | 0.6715 | 0.8938 | 0.8225 | 0.4834 | 0.8119 |

| | Cell line | | | | |
|---|---|---|---|---|---|
| | T47D | HCC1419 | MDA-MB-453 | MDA-MB-330 | BT474 | 184A |
| $GI_{50}$ (μM) | 2.516 | 10.04 | 2.299 | 7.016 | 8.585 | 1.59 |

EXAMPLE 4

TTK Overexpression in Basal-like Breast Cancer Cells

Figure 3:
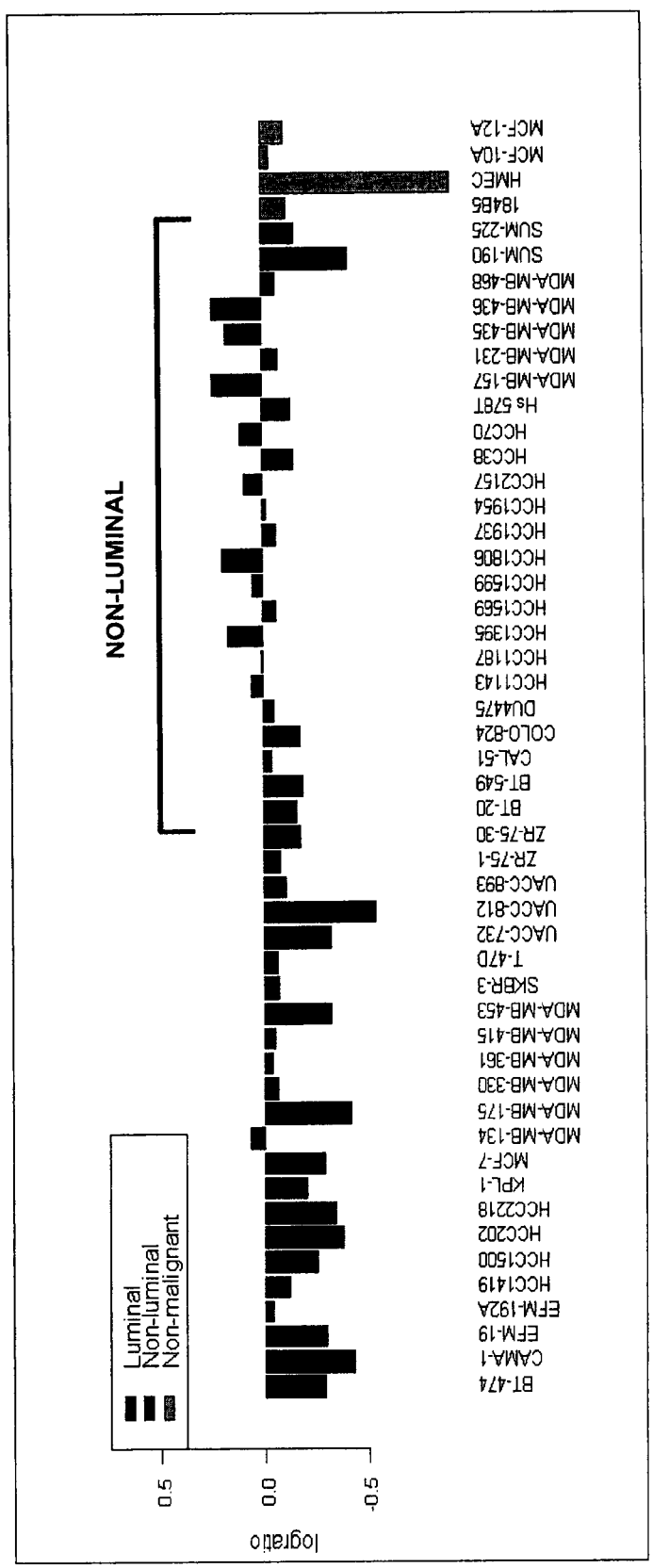
FIG. 3 is a graph depicting microarray expression data illustrating that TTK RNA is overexpressed more frequently and to a greater extent in non-luminal breast cancer cell lines than in luminal, non-malignant breast cancer cell lines, relative to normal breast cell lines or non-malignant breast cells.
Figure 4:
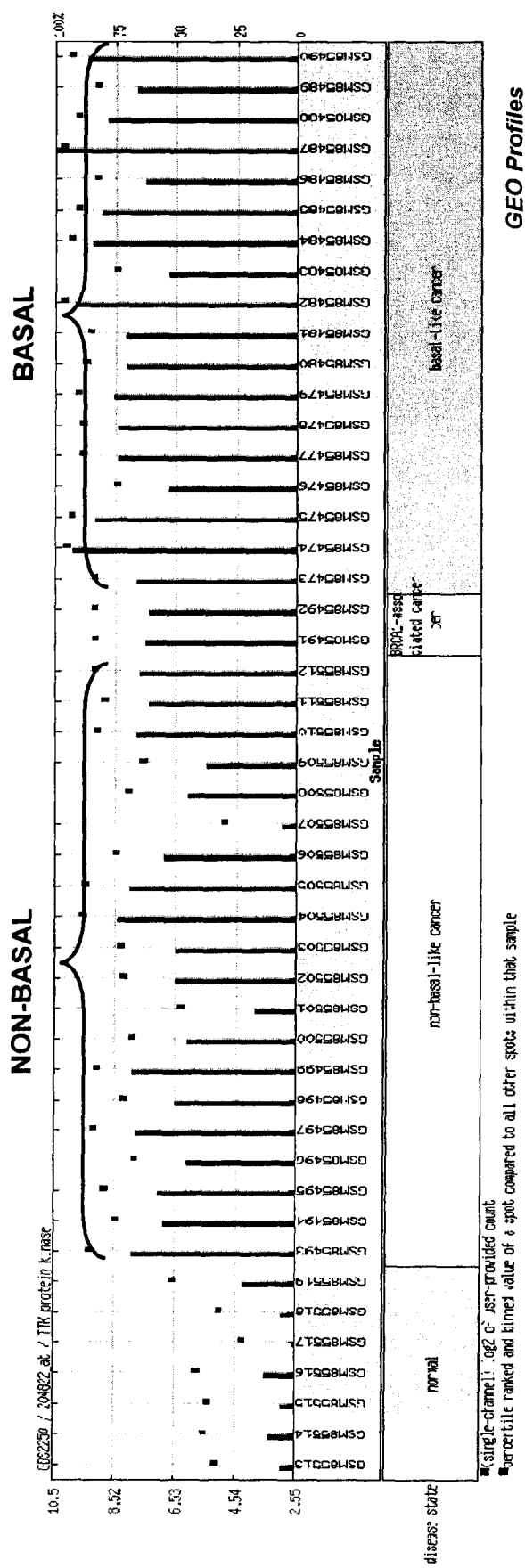
FIG. 4 is a microarray gene expression profile illustrating TTK RNA overexpression in non-basal-like, BRCA1-associated and basal-like cancer cell lines relative to normal breast cell lines. TTK RNA expression is shown to be highest in basal-like breast cancer cell lines.

The inventor have discovered an association between TTK overexpression and basal-like breast cancers and soft-tissue sarcomas. In particular, overexpression of TTK was detected in non-luminal (e.g., basal-like, non-basal-like, HER-2 positive/ER-negative) breast cancer cells more frequently than in luminal (e.g., luminal A, luminal B) or non-malignant breast cells (FIG. 3). Of the non-luminal breast cancer cell lines evaluated, TTK overexpression was detected most frequently in basal-like breast cancer cells (Table 4), which also displayed the highest levels of TTK protein expression (FIG. 4).

TABLE 4

TTK is overexpressed in different breast cancer subtypes

| | % ↑ OVERALL | % ↑ BASAL | % ↑ HER2/ER- | % ↑ LUMINAL A | % ↑ LUMINAL B |
|---|---|---|---|---|---|
| TTK 6q I4.1 | 38 | 85 | 38 | 6 | 18 |

Perou Dataset: % increase in tumors vs. normal samples.

Figure 5:
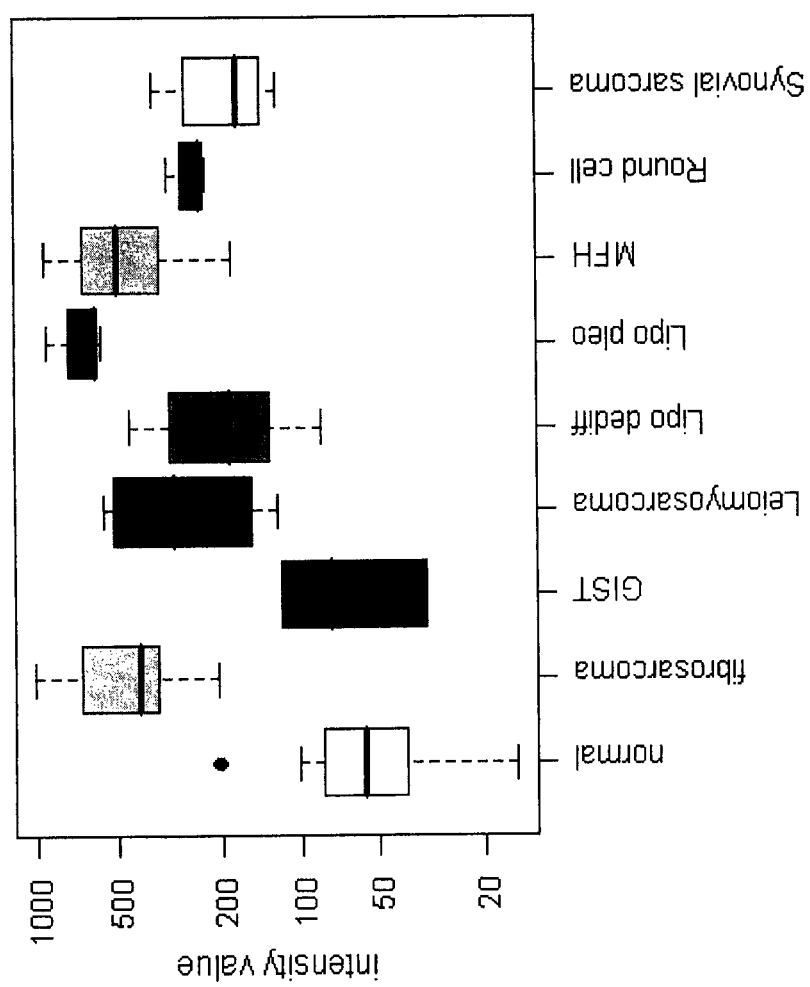
FIG. 5 is a graph illustrating TTK RNA expression levels in different normal soft tissue (normal, GIST) and soft tissue sarcoma samples (fibrosarcoma, leiomyosarcoma, Lipo dediff, Lipo pleo, MFH, Round cell, Synovial sarcoma). Increased TTK RNA levels were observed in sarcoma samples relative to samples from physiologically normal tissues.

Microarray expression analysis revealed elevated TTK gene expression in several soft-tissue sarcoma samples derived from various tissues, as compared to TTK gene expression in physiologically normal tissues (FIG. 5).

These results indicate that TTK is a target for cancer therapy, particularly basal-like breast cancer therapy and soft tissue sarcoma therapy.

EXAMPLE 5

RNAi Silencing of TTK Suppresses Tumor Growth In Vivo

A double-stranded oligonucleotide encoding a human TTK gene-specific shRNA (sense insert sequence 5'-GCAGUCAUGCCCAUUUGGAA-3' (SEQ ID NO:11)) was ligated into the RNAi-Ready-pSIREN-RetroQ-ZsGreen retroviral vector (Clontech). Amphotropic-Phoenix packaging cells (ATCC, Manassas, Va.) were transiently transfected with either control RNAi-Ready-pSIREN-RetroQ-ZsGreen-shLUC (Clontech) or RNAi-Ready-pSIREN-RetroQ-ZsGreen-shTTK using FuGENE 6 transfection reagent (Roche Diagnostics, Indianapolis, Ind.). Culture supernatants were collected 2 days after transfection and filtered through 0.45-μm pore-size filters. MDA-MB-468 breast cancer cells (ATCC, Manassas, Va.) were infected with retroviruses by culturing the cells for 24 hours in 1:1 *Phoenix* conditioned media (Dulbecco's Modified Eagle's Media, 10% FCS, supplemented with 8 μg/ml Polybrene; Sigma-Aldrich). This transfection process was repeated three times to increase the transfection efficiency. One day after the final infection, the RNAi-Ready-pSIREN-RetroQ-ZsGreen-shLUC and RNAi-Ready-pSIREN-RetroQ-ZsGreen-shTTK infected cancer cells were trypsinized, counted and injected subcutaneously into the left and right hindlimb, respectively, of nude mice at concentrations of $2.5 \times 10^6$ cells (5 mice per group). The infected cells were also analyzed for TTK expression by RT-PCR using TTK-specific primers. The tumors were measured and viable tumor area was calculated twice weekly for approximately 10 weeks.

Figure 17A:
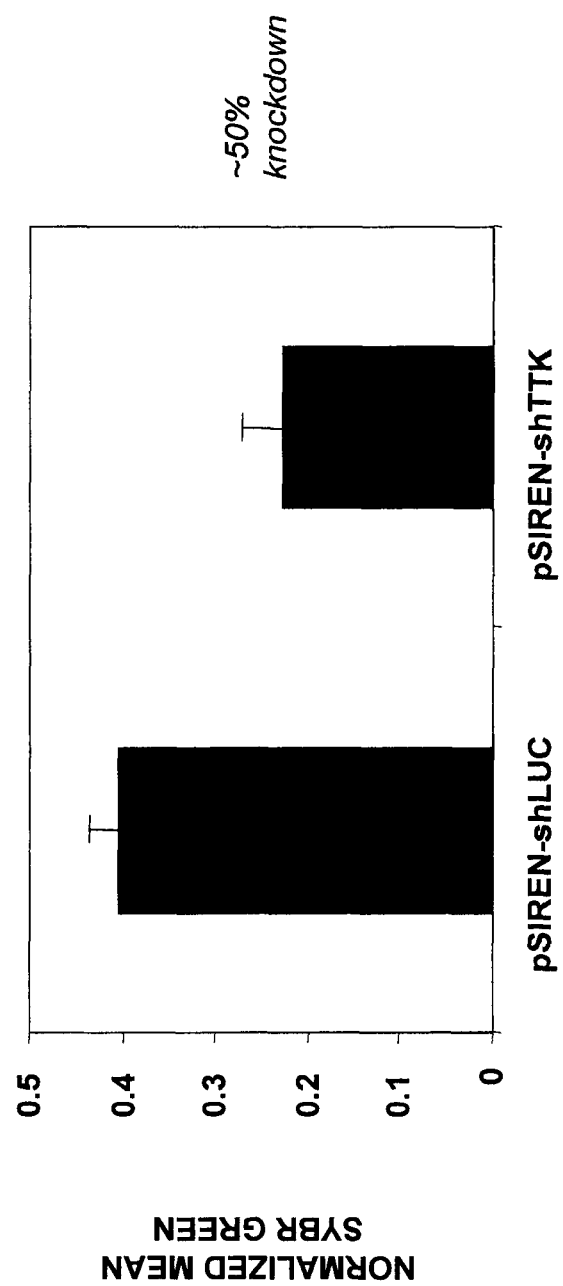
FIG. 17A is a graph depicting normalized TTK transcript levels in MDA-MB-468 cells infected with constructs expressing either control shRNA (pSIREN-shLUC) or TTK shRNA (pSIREN-shTTK). TTK transcript levels in MDA-MB-468 cells expressing TTK shRNA were reduced by about 50% relative to controls.
Figure 17B:
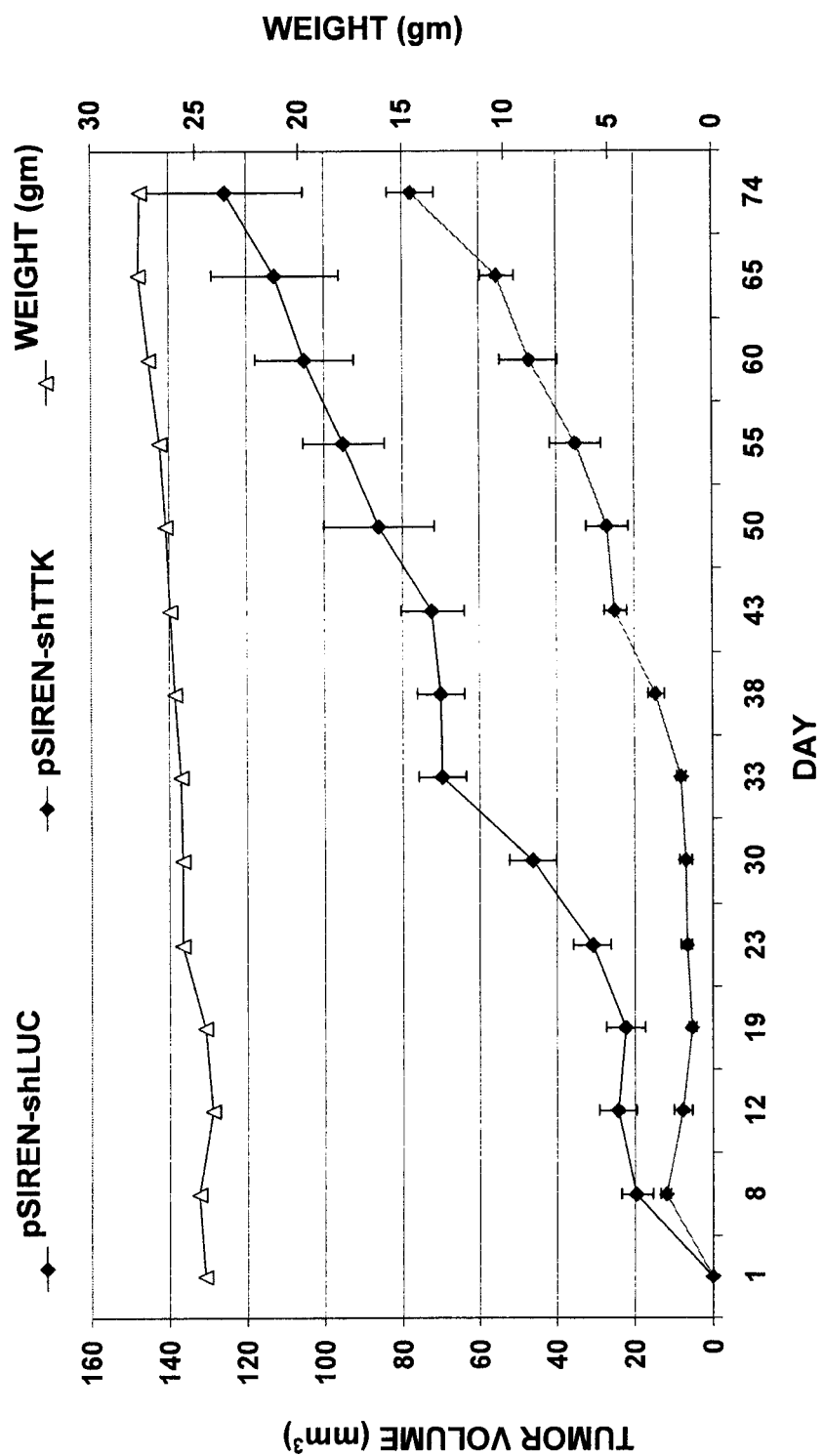
FIG. 17B is a graph depicting significant suppression of tumor growth in mice that were injected with MDA-MB-468 cells infected with a construct expressing TTK shRNA (pSIREN-shTTK) relative to mice injected with MDA-MB-468 cells infected with a construct expressing control shRNA (pSIREN-shLUC); $2.5 \times 10^6$ pSIREN-shLUC (control) and pSIREN-shTTK infected MDA-MB-468 cells were injected subcutaneously into the left and right hindlimb, respectively of nude mice (n=5).

Infection of MDA-MB-468 cells with the TTK shRNA-encoding construct led to the reduction of TTK expression in these cells by approximately 50% compared to that of the control cells (FIG. 17A). Furthermore, reduction of TTK mRNA levels resulted in a significant suppression of tumor growth in a mouse xenograft model (FIG. 17B). Taken together, these results suggest that inhibition of TTK activity in cancer cells inhibits tumor growth in tumors that express TTK.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for treating TTK positive non-luminal breast cancer in a mammalian subject, comprising administering to the subject a therapeutically effective amount of a TTK antagonist, wherein said cancer is HER-2 positive breast cancer.

2. The method of claim 1, wherein the TKK antagonist is selected from the group consisting of a small interfering ribonucleic acid (siRNA) or an antisense oligonucleotide.

3. The method of claim 1, wherein the TTK antagonist is selected from the group consisting of an antibody, an antigen-binding fragment of an antibody, or a peptide.

4. The method of claim 1, wherein the TTK antagonist is selected from the group consisting of a small molecule or a peptidomimetic.

5. The method of claim 1, further comprising administering one or more other therapeutic agents.

6. The method of claim 5, wherein a HER-2 antagonist is also administered.

7. The method of claim 6, wherein said HER-2 antagonist is trastuzumab.

8. The method of claim 6, wherein said HER-2 positive breast cancer is estrogen receptor (ER) negative.

9. The method of claim 1, wherein said tumor is a metastatic tumor.

10. The method of claim 1, wherein said HER-2 positive tumor is estrogen receptor (ER) negative.

11. A method of treating a TTK positive breast cancer in a mammalian subject, wherein said breast cancer is HER-2 positive and ER negative, comprising administering to the subject a therapeutically effective amount of a TTK antagonist.

12. The method of claim 11, wherein the TKK antagonist is selected from the group consisting of a siRNA or an antisense oligonucleotide.

13. The method of claim 11, wherein the TTK antagonist is selected from the group consisting of an antibody, an antigen-binding fragment of an antibody, or a peptide.

14. The method of claim 11, wherein the TTK antagonist is selected from the group consisting of a small molecule or a peptidomimetic.

15. The method of claim 11, further comprising administering a HER-2 antagonist.

16. The method of claim 15, wherein the HER-2 antagonist is trastuzumab.

* * * * *

UNITED STATES PATENT AND TRADEMARK OFFICE
CERTIFICATE OF CORRECTION

PATENT NO. : 8,492,356 B2
APPLICATION NO. : 12/808159
DATED : July 23, 2013
INVENTOR(S) : Guohua Pan It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 305 days.

Signed and Sealed this
Fifth Day of November, 2013

Teresa Stanek Rea
*Deputy Director of the United States Patent and Trademark Office*

SEQUENCE LISTING

```
<160> NUMBER OF SEQ ID NOS: 11

<210> SEQ ID NO 1
<211> LENGTH: 3866
<212> TYPE: DNA
<213> ORGANISM: Homo sapiens

<400> SEQUENCE: 1
ggaattcctt tttttttttt tttgagatgg agtttcactc ttgttggcca ggctggagtg      60
caatggcaca atctcagctt actgcaacct ccgcctcccg ggttcaagcg attctcctgc     120
ctcagcctct caagtagctg ggattacagg catgtgccac caccctggc taactaattt     180 cttttctatt tagtagagat ggggtttcac catgttggtc aggctggtct tgaactcctg     240
acctcaggtg atccacttgc cttggcctcc caaagtgcta ggattacagc cgtgaaactg     300
tgcctggctg attcttttt tgttgttgga tttttgaaac agggtctccc ttggtcgccc     360
aggctggagt gcagtggtgc gatcttggct cactataacc tccacctcct ggtttcaagt     420
gatcctccca ctttagcctc ctgagtagct gtgattacag gcgtgcacca ccacacccgg     480 ctaattttg tatttttatt agagacaggg tttcaccatg ttggccaggc tgttctcaaa     540
ctcctggact caagggatcc gcctgcctcc acttcccaaa gtcccgagat tacaggtgtg     600
agtcaccatg cctgacctta taattcttaa gtcatttttt ctggtccatt tcttccttag     660
ggtcctcaca acaaatctgc attaggcggt acaataatcc ttaacttcat gattcacaaa     720
aggaagatga agtgattcat gatttagaaa ggggaagtag taagcccact gcacactcct     780
ggatgatgat cctaaatcca gatacagtaa aaatggggta tgggaaggta gaatacaaaa     840
tttggtttaa attaattatc taaatatcta aaaacatttt tggatacatt gttgatgtga     900
atgtaagact gtacagactt cctagaaaac agtttgggtt ccatcttttc atttccccag     960
tgcagttttc tgtagaaatg gaatccgagg atttaagtgg cagagaattg acaattgatt    1020
ccataatgaa caaagtgaga gacattaaaa ataagtttaa aaatgaagac cttactgatg    1080
```

```
aactaagctt gaataaaatt tctgctgata ctacagataa ctcgggaact gttaaccaaa    1140
ttatgatgat ggcaaacaac ccagaggact ggttgagttt gttgctcaaa ctagagaaaa    1200
acagtgttcc gctaagtgat gctcttttaa ataaattgat tggtcgttac agtcaagcaa    1260
ttgaagcgct tcccccagat aaatatggcc aaaatgagag ttttgctaga attcaagtga    1320
gatttgctga attaaaagct attcaagagc cagatgatgc acgtgactac tttcaaatgg    1380
ccagagcaaa ctgcaagaaa tttgcttttg ttcatatatc ttttgcacaa tttgaactgt    1440
cacaaggtaa tgtcaaaaaa agtaaacaac ttcttcaaaa agctgtagaa cgtggagcag    1500
taccactaga aatgctggaa attgccctgc ggaatttaaa cctccaaaaa aagcagctgc    1560
tttcagagga ggaaaagaag aatttatcag catctacggt attaactgcc caagaatcat    1620
tttccggttc acttgggcat ttacagaata ggaacaacag ttgtgattcc agaggacaga    1680
ctactaaagc caggttttta tatggagaga acatgccacc acaagatgca gaaataggtt    1740
accggaattc attgagacaa actaacaaaa ctaaacagtc atgcccattt ggaagagtcc    1800
cagttaacct tctaaatagc ccagattgtg atgtgaagac agatgattca gttgtacctt    1860
gttttatgaa aagacaaacc tctagatcag aatgccgaga tttggttgtg cctgatctaa    1920
aaccaagtgg aaatgattcc tgtgaattaa gaaatttaaa gtctgttcaa aatagtcatt    1980
tcaaggaacc tctggtgtca gatgaaaaga gttctgaact tattattact gattcaataa    2040
ccctgaagaa taaaacggaa tcaagtcttc tagctaaatt agaagaaact aaagagtatc    2100
aagaaccaga ggttccagag agtaaccaga acagtggcca agctaagaga agtcagagt     2160 gtattaacca gaatcctgct gcatcttcaa atcactggca gattccggag ttagcccgaa    2220
aagttaatac agagcagaaa cataccactt tgagcaacc tgtcttttca gtttcaaaac    2280
agtcaccacc aatatcaaca tctaaatggt ttgacccaaa atctatttgt aagacaccaa    2340
gcagcaatac cttggatgat tacatgagct gttttagaac tccagttgta aagaatgact    2400
ttccacctgc ttgtcagttg tcaacacctt atggccaacc tgcctgtttc agcagcaac    2460 agcatcaaat acttgccact ccacttcaaa atttacaggt tttagcatct tcttcagcaa    2520
atgaatgcat ttcggttaaa ggaagaattt attccatatt aaagcagata ggaagtggag    2580
gttcaagcaa ggtatttcag gtgttaaatg aaaagaaaca gatatatgct ataaaatatg    2640
tgaacttaga agaagcagat aaccaaactc ttgatagtta ccggaacgaa atagcttatt    2700
tgaataaact acaacaacac agtgataaga tcatccgact ttatgattat gaaatcacgg    2760
accagtacat ctcatggta atggagtgtg gaaatattga tcttaatagt tggcttaaaa    2820
agaaaaaatc cattgatcca tgggaacgca agagttactg gaaaaatatg ttagaggcag    2880
ttcacacaat ccatcaacat ggcattgttc acagtgatct taaaccagct aactttctga    2940
tagttgatgg aatgctaaag ctaattgatt ttgggattgc aaaccaaatg caaccagata    3000
caacaagtgt tgttaaagat tctcaggttg cacagttaa ttatatgcca ccagaagcaa     3060
tcaaagatat gtcttcctcc agagagaatg ggaaatctaa gtcaaagata agccccaaaa    3120
gtgatgtttg gtccttagga tgtattttgt actatatgac ttacgggaaa acaccatttc    3180
agcagataat taatcagatt tctaaattac atgccataat tgatcctaat catgaaattg    3240
aatttcccga tattccagag aaagatcttc aagatgtgtt aaagtgttgt ttaaaaaggg    3300
acccaaaaca gaggatatcc attcctgagc tcctggctca tccatatgtt caaattcaaa    3360
ctcatccagt taaccaaatg gccaagggaa ccactgaaga aatgaaatat gttctgggcc    3420
aacttgttgg tctgaattct cctaactcca ttttgaaagc tgctaaaact ttatatgaac    3480
```

-continued

```
actatagtgg tggtgaaagt cataattctt catcctccaa gacttttgaa aaaaaaaggg   3540
gaaaaaaatg atttgcagtt attcgtaatg tcagatagga ggtataaaat atattggact   3600
gttatactct tgaatccctg tggaaatcta catttgaaga caacatcact ctgaagtgtt   3660
atcagcaaaa aaaattcagt gagattatct ttaaaagaaa actgtaaaaa tagcaaccac   3720
ttatggcact gtatatattg tagacttgtt ttctctgttt tatgctcttg tgtaatctac   3780
ttgacatcat tttactcttg gaatagtggg tggatagcaa gtatattcta aaaaactttg   3840
taaataaagt tttgtggcta aaatga                                         3866
```

<210> SEQ ID NO 2
<211> LENGTH: 857
<212> TYPE: PRT
<213> ORGANISM: Homo sapiens

<400> SEQUENCE: 2

```
Met Glu Ser Glu Asp Leu Ser Gly Arg Glu Leu Thr Ile Asp Ser Ile
 1               5                  10                  15

Met Asn Lys Val Arg Asp Ile Lys Asn Lys Phe Lys Asn Glu Asp Leu
            20                  25                  30

Thr Asp Glu Leu Ser Leu Asn Lys Ile Ser Ala Asp Thr Thr Asp Asn
        35                  40                  45

Ser Gly Thr Val Asn Gln Ile Met Met Met Ala Asn Asn Pro Glu Asp
    50                  55                  60

Trp Leu Ser Leu Leu Lys Leu Glu Lys Asn Ser Val Pro Leu Ser
65                  70                  75                  80

Asp Ala Leu Leu Asn Lys Leu Ile Gly Arg Tyr Ser Gln Ala Ile Glu
                85                  90                  95

Ala Leu Pro Pro Asp Lys Tyr Gly Gln Asn Glu Ser Phe Ala Arg Ile
            100                 105                 110

Gln Val Arg Phe Ala Glu Leu Lys Ala Ile Gln Glu Pro Asp Asp Ala
        115                 120                 125

Arg Asp Tyr Phe Gln Met Ala Arg Ala Asn Cys Lys Lys Phe Ala Phe
    130                 135                 140

Val His Ile Ser Phe Ala Gln Phe Glu Leu Ser Gln Gly Asn Val Lys
145                 150                 155                 160

Lys Ser Lys Gln Leu Leu Gln Lys Ala Val Glu Arg Gly Ala Val Pro
                165                 170                 175

Leu Glu Met Leu Glu Ile Ala Leu Arg Asn Leu Asn Leu Gln Lys Lys
            180                 185                 190

Gln Leu Leu Ser Glu Glu Lys Lys Asn Leu Ser Ala Ser Thr Val
        195                 200                 205

Leu Thr Ala Gln Glu Ser Phe Ser Gly Ser Leu Gly His Leu Gln Asn
    210                 215                 220

Arg Asn Asn Ser Cys Asp Ser Arg Gly Gln Thr Thr Lys Ala Arg Phe
225                 230                 235                 240

Leu Tyr Gly Glu Asn Met Pro Pro Gln Asp Ala Glu Ile Gly Tyr Arg
                245                 250                 255

Asn Ser Leu Arg Gln Thr Asn Lys Thr Lys Gln Ser Cys Pro Phe Gly
            260                 265                 270

Arg Val Pro Val Asn Leu Leu Asn Ser Pro Asp Cys Asp Val Lys Thr
        275                 280                 285

Asp Asp Ser Val Val Pro Cys Phe Met Lys Arg Gln Thr Ser Arg Ser
    290                 295                 300

Glu Cys Arg Asp Leu Val Val Pro Gly Ser Lys Pro Ser Gly Asn Asp
```

```
            305                 310                 315                 320
Ser Cys Glu Leu Arg Asn Leu Lys Ser Val Gln Asn Ser His Phe Lys
                325                 330                 335

Glu Pro Leu Val Ser Asp Glu Lys Ser Ser Glu Leu Ile Ile Thr Asp
                340                 345                 350

Ser Ile Thr Leu Lys Asn Lys Thr Glu Ser Ser Leu Leu Ala Lys Leu
                355                 360                 365

Glu Glu Thr Lys Glu Tyr Gln Glu Pro Glu Val Pro Glu Ser Asn Gln
                370                 375                 380

Lys Gln Trp Gln Ser Lys Arg Lys Ser Glu Cys Ile Asn Gln Asn Pro
385                 390                 395                 400

Ala Ala Ser Ser Asn His Trp Gln Ile Pro Glu Leu Ala Arg Lys Val
                405                 410                 415

Asn Thr Glu Gln Lys His Thr Thr Phe Glu Gln Pro Val Phe Ser Val
                420                 425                 430

Ser Lys Gln Ser Pro Pro Ile Ser Thr Ser Lys Trp Phe Asp Pro Lys
                435                 440                 445

Ser Ile Cys Lys Thr Pro Ser Ser Asn Thr Leu Asp Asp Tyr Met Ser
450                 455                 460

Cys Phe Arg Thr Pro Val Val Lys Asn Asp Phe Pro Pro Ala Cys Gln
465                 470                 475                 480

Leu Ser Thr Pro Tyr Gly Gln Pro Ala Cys Phe Gln Gln Gln His
                485                 490                 495

Gln Ile Leu Ala Thr Pro Leu Gln Asn Leu Gln Val Leu Ala Ser Ser
                500                 505                 510

Ser Ala Asn Glu Cys Ile Ser Val Lys Gly Arg Ile Tyr Ser Ile Leu
                515                 520                 525

Lys Gln Ile Gly Ser Gly Gly Ser Ser Lys Val Phe Gln Val Leu Asn
                530                 535                 540

Glu Lys Lys Gln Ile Tyr Ala Ile Lys Tyr Val Asn Leu Glu Glu Ala
545                 550                 555                 560

Asp Asn Gln Thr Leu Asp Ser Tyr Arg Asn Glu Ile Ala Tyr Leu Asn
                565                 570                 575

Lys Leu Gln Gln His Ser Asp Lys Ile Ile Arg Leu Tyr Asp Tyr Glu
                580                 585                 590

Ile Thr Asp Gln Tyr Ile Tyr Met Val Met Glu Cys Gly Asn Ile Asp
                595                 600                 605

Leu Asn Ser Trp Leu Lys Lys Lys Ser Ile Asp Pro Trp Glu Arg
                610                 615                 620

Lys Ser Tyr Trp Lys Asn Met Leu Glu Ala Val His Thr Ile His Gln
625                 630                 635                 640

His Gly Ile Val His Ser Asp Leu Lys Pro Ala Asn Phe Leu Ile Val
                645                 650                 655

Asp Gly Met Leu Lys Leu Ile Asp Phe Gly Ile Ala Asn Gln Met Gln
                660                 665                 670

Pro Asp Thr Thr Ser Val Val Lys Asp Ser Gln Val Gly Thr Val Asn
                675                 680                 685

Tyr Met Pro Pro Glu Ala Ile Lys Asp Met Ser Ser Ser Arg Glu Asn
                690                 695                 700

Gly Lys Ser Lys Ser Lys Ile Ser Pro Lys Ser Asp Val Trp Ser Leu
705                 710                 715                 720

Gly Cys Ile Leu Tyr Tyr Met Thr Tyr Gly Lys Thr Pro Phe Gln Gln
                725                 730                 735
```

-continued

```
Ile Ile Asn Gln Ile Ser Lys Leu His Ala Ile Ile Asp Pro Asn His
        740                 745                 750

Glu Ile Glu Phe Pro Asp Ile Pro Glu Lys Asp Leu Gln Asp Val Leu
            755                 760                 765

Lys Cys Cys Leu Lys Arg Asp Pro Lys Gln Arg Ile Ser Ile Pro Glu
770                 775                 780

Leu Leu Ala His Pro Tyr Val Gln Ile Gln Thr His Pro Val Asn Gln
785                 790                 795                 800

Met Ala Lys Gly Thr Thr Glu Glu Met Lys Tyr Val Leu Gly Gln Leu
                805                 810                 815

Val Gly Leu Asn Ser Pro Asn Ser Ile Leu Lys Ala Ala Lys Thr Leu
            820                 825                 830

Tyr Glu His Tyr Ser Gly Gly Glu Ser His Asn Ser Ser Ser Ser Lys
        835                 840                 845

Thr Phe Glu Lys Lys Arg Gly Lys Lys
    850                 855

<210> SEQ ID NO 3
<211> LENGTH: 19
<212> TYPE: RNA
<213> ORGANISM: Artificial Sequence
<220> FEATURE:
<223> OTHER INFORMATION: siRNA

<400> SEQUENCE: 3
gcaauaccuu ggaugauua                                                    19

<210> SEQ ID NO 4
<211> LENGTH: 19
<212> TYPE: RNA
<213> ORGANISM: Artificial Sequence
<220> FEATURE:
<223> OTHER INFORMATION: siRNA

<400> SEQUENCE: 4
gguauuaacu gcccaagaa                                                    19

<210> SEQ ID NO 5
<211> LENGTH: 19
<212> TYPE: RNA
<213> ORGANISM: Artificial Sequence
<220> FEATURE:
<223> OTHER INFORMATION: siRNA

<400> SEQUENCE: 5
gcacgugacu acuuucaaa                                                    19

<210> SEQ ID NO 6
<211> LENGTH: 19
<212> TYPE: RNA
<213> ORGANISM: Artificial Sequence
<220> FEATURE:
<223> OTHER INFORMATION: siRNA

<400> SEQUENCE: 6
gauaagauca uccgacuuu                                                    19

<210> SEQ ID NO 7
<211> LENGTH: 21
<212> TYPE: DNA
<213> ORGANISM: Artificial Sequence
<220> FEATURE:
<223> OTHER INFORMATION: forward amplification primer
```

-continued

```
<400> SEQUENCE: 7
tgatggcaaa caacccagag g                                              21

<210> SEQ ID NO 8
<211> LENGTH: 22
<212> TYPE: DNA
<213> ORGANISM: Artificial Sequence
<220> FEATURE:
<223> OTHER INFORMATION: reverse amplification primer

<400> SEQUENCE: 8
ttgcttgact gtaacgacca at                                             22

<210> SEQ ID NO 9
<211> LENGTH: 21
<212> TYPE: DNA
<213> ORGANISM: Artificial Sequence
<220> FEATURE:
<223> OTHER INFORMATION: forward amplification primer

<400> SEQUENCE: 9
ggcactcttc cagccttcct t                                              21

<210> SEQ ID NO 10
<211> LENGTH: 20
<212> TYPE: DNA
<213> ORGANISM: Artificial Sequence
<220> FEATURE:
<223> OTHER INFORMATION: reverse amplification primer

<400> SEQUENCE: 10
tctccttctg catcctgtcg                                                20

<210> SEQ ID NO 11
<211> LENGTH: 20
<212> TYPE: RNA
<213> ORGANISM: Artificial Sequence
<220> FEATURE:
<223> OTHER INFORMATION: shRNA

<400> SEQUENCE: 11
gcagucaugc ccauuuggaa                                                20
```